US010206580B2

United States Patent
Lee et al.

(10) Patent No.: US 10,206,580 B2
(45) Date of Patent: Feb. 19, 2019

(54) FULL-FIELD OCT SYSTEM USING WAVELENGTH-TUNABLE LASER AND THREE-DIMENSIONAL IMAGE CORRECTION METHOD

(71) Applicants: KOH YOUNG TECHNOLOGY INC., Seoul (KR); INDUSTRY-UNIVERSITY COOPERATION FOUNDATION HANYANG UNIVERSITY, Seoul (KR)

(72) Inventors: Hyun Ki Lee, Daegu (KR); Hong Ki Yoo, Seoul (KR); Chang Soo Kim, Seoul (KR); Hyeong Soo Nam, Seoul (KR)

(73) Assignees: KOH YOUNG TECHNOLOGY INC., Seoul (KR); INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 15/771,931

(22) PCT Filed: Oct. 19, 2016

(86) PCT No.: PCT/KR2016/011733
§ 371 (c)(1),
(2) Date: Apr. 27, 2018

(87) PCT Pub. No.: WO2017/073945
PCT Pub. Date: May 4, 2017

(65) Prior Publication Data
US 2018/0344163 A1   Dec. 6, 2018

(30) Foreign Application Priority Data

Oct. 29, 2015 (KR) .................. 10-2015-0151399
Aug. 12, 2016 (KR) .................. 10-2016-0103249

(51) Int. Cl.
*G01B 9/02* (2006.01)
*A61B 5/00* (2006.01)
*G01N 21/45* (2006.01)

(52) U.S. Cl.
CPC .......... *A61B 5/0066* (2013.01); *A61B 5/0077* (2013.01); *G01B 9/02041* (2013.01);
(Continued)

(58) Field of Classification Search
CPC ............. A61B 5/0066; G01B 9/02041; G01B 9/02083; G01B 9/02091; G01B 9/0209;
(Continued)

(56) References Cited

U.S. PATENT DOCUMENTS 6,680,780 B1 *  1/2004  Fee ........................ A61B 5/40
                                                         356/498
8,204,300 B2 *  6/2012  Sugita .................... A61B 3/102
                                                         356/479

(Continued)

FOREIGN PATENT DOCUMENTS

JP    2008-128710     6/2008
KR  10-2008-0065252   7/2008

(Continued)

OTHER PUBLICATIONS

International Search Report for International Application No. PCT/KR2016/011733, dated Jan. 23, 2017.

*Primary Examiner* — Tarifur R Chowdhury
*Assistant Examiner* — Jonathon Cook
(74) *Attorney, Agent, or Firm* — Kile Park Reed & Houtteman PLLC

(57) ABSTRACT

The present disclosure provides a full-field OCT system using a wavelength-tunable laser, which can observe peaks of a short-time A-line profile corresponding to each time point at which interference images of an object to be
(Continued)

measured are acquired, so as to measure a depth direction movement of the object to be measured, and can correct the phases of interference signals on the basis of the measured depth direction movement, so as to generate an OCT image which is compensated for the depth direction movement.

9 Claims, 20 Drawing Sheets

(52) U.S. Cl.
CPC ..... *G01B 9/02083* (2013.01); *G01B 9/02091* (2013.01); *G01N 21/45* (2013.01)

(58) Field of Classification Search
CPC ............ G01B 9/02002; G01B 9/02004; G01B 9/02005; G01B 9/02077
USPC .................................................. 356/479, 497
See application file for complete search history.

(56) References Cited

U.S. PATENT DOCUMENTS

| | | | |
|---|---|---|---|
| 8,632,181 B2* | 1/2014 | Bublitz | A61B 3/1005 351/209 |
| 2008/0117430 A1 | 5/2008 | Terakawa et al. | |
| 2009/0244485 A1* | 10/2009 | Walsh | A61B 3/1005 351/221 |
| 2010/0027019 A1 | 2/2010 | Suehira | |
| 2011/0299034 A1* | 12/2011 | Walsh | A61B 3/102 351/206 |
| 2013/0003077 A1 | 1/2013 | Suehira et al. | |
| 2014/0092392 A1* | 4/2014 | Hillmann | G01N 21/4795 356/479 |

FOREIGN PATENT DOCUMENTS

| | | |
|---|---|---|
| KR | 10-2013-0000415 | 1/2013 |
| KR | 10-2013-0091911 | 8/2013 |

* cited by examiner

FULL-FIELD OCT SYSTEM USING WAVELENGTH-TUNABLE LASER AND THREE-DIMENSIONAL IMAGE CORRECTION METHOD

TECHNICAL FIELD

The present disclosure relates to a full-field OCT (Optical Coherence Tomography) system using a wavelength-tunable laser and an image correction method of the full-field OCT system.

BACKGROUND

OCT is a medical imaging technique that can capture cross-sectional images of biological tissues with a resolution of about 10~30 μm. An OCT system can create a three-dimensional OCT image of a measurement target, using interference images formed by interference between reference light, that is created when a laser beam is reflected by a reference mirror, and reflective light that is created when the laser beam is reflected by the measurement target.

OCT systems can be classified into, depending on the method of radiating a laser beam to a measurement target, a single point scanning OCT system and a full-field OCT system. The single point scanning OCT system can create an OCT image of a measurement target, using interference images captured by horizontally scanning a laser beam that is radiated to a single point on the measurement target. The full-field OCT system can create an OCT image of a measurement target, using interference images captured by radiating a laser beam having a predetermined area to the measurement target without horizontally scanning the laser beam.

As described above, since the full-field OCT system can obtain interference signals for a predetermined area at a time from captured interference images without a scanning process in horizontal direction, the OCT image can be created quickly. However, when comparing the measurement time for obtaining interference signals for one point on a measurement target, the full-field OCT system may take more time than the single point scanning OCT system. Accordingly, if the measurement target moves while the full-field OCT system is capturing interference images, the interference signals are easily influenced by movement of the measurement target. Further, an OCT image created using interference signals that include the movement of the measurement target may include artifacts resulting from the movement of the measurement target.

SUMMARY

A problem to be solved by the present disclosure is to provide a method that can measure depth-directional movement and horizontal movement of a measurement target and a full-field OCT system using such method.

Another problem to be solved by the present disclosure is to provide a method that can compensate for the movement of a measurement target in an OCT image using measurement results of depth-directional movement and horizontal movement of the measurement target, and a full-field OCT system using such method.

A full-field OCT system according to an embodiment of the present disclosure may include an image processor that determines depth-directional movement of a measurement target and compensates the depth-directional movement of the measurement target based on a plurality of interference images that are formed by interference between reference light, that is created when a laser beam having wavelengths corresponding to each wave number is reflected by a reference mirror, and reflective light that is created when the laser beam is reflected by the measurement target, wherein the image processor may be configured to obtain interference intensities corresponding to each wave number included in each wave number domain for a specific point on the measurement target from interference images corresponding to each wave number included in each wave number domain among the plurality of interference images, obtain short-time A-line profiles corresponding to each wave number domain based on the obtained interference intensities, obtain depth values corresponding to each wave number domain from each short-time A-line profiles, and determine the depth-directional movement of the measurement target based on changes of the obtained depth values.

According to an embodiment, when the interference images corresponding to each wave number included in each wave number domain are selected by sequentially applying a sliding wave number domain window having a predetermined size to the plurality of interference images, the image processor may be further configured to obtain the interference intensities corresponding to each wave number included in each wave number domain for the specific point on the measurement target from the selected interference images, and obtain the short-time A-line profiles corresponding to each wave number domain by performing short-time Fourier transform on the obtained interference intensities in each of wave number domain.

According to an embodiment, the depth values may correspond to each peak of the short-time A-line profiles.

According to an embodiment, the image processor may be configured to create a depth-directional movement function corresponding to depth-directional movement of the measurement target, create a phase compensation function corresponding to the depth-directional movement by integrating the depth-directional movement function, extract interference intensities at each identical point in the plurality of interference images, and compensate for the depth-directional movement of the measurement target by compensating for the phases of interference signals indicating the distribution of the extracted interference intensities in a wave number domain for each identical point based on the phase compensation function.

According to an embodiment, the full-field OCT system may further include an interferometer configured to create the plurality of interference images corresponding to each wave number, wherein the interferometer may include: a wavelength-tunable laser configured to radiate a laser beam having wavelengths corresponding to each wave number by tuning a wavelength; a reference mirror; a beam splitter configured to transmit a portion of the laser beam from the wavelength-tunable laser toward the measurement target and reflect the other portion of the laser beam toward the reference mirror; and an imaging device configured to create the plurality of interference images by receiving the reflective light and the reference light from the beam splitter.

A method of determining depth-directional movement of a measurement target and compensating for the depth-directional movement of the measurement target in a full-field OCT system according to an embodiment of the present disclosure may include the steps of: receiving, by an image processor, a plurality of interference images that are formed by interference between reference light that is created when a laser beam having wavelengths corresponding to each wave number is reflected by a reference mirror and reflective light that is created when the laser beam is reflected by the measurement target; obtaining, by the image processor, interference intensities corresponding to each wave number included in each wave number domain for a specific point on the measurement target from interference images corresponding to each wave number included in each wave number domain among the plurality of interference images; obtaining, by the image processor, short-time A-line profiles corresponding to each wave number domain based on the obtained interference intensities; obtaining, by the image processor, depth values corresponding to each wave number from the short-time A-line profiles; and determining, by the image processor, the depth-directional movement of the measurement target based on changes of the obtained depth values.

According to an embodiment, when the interference images corresponding to each wave number included in each wave number domain are selected by sequentially applying a sliding wave number domain window having a predetermined size to the plurality of interference images, the step of obtaining, by the image processor, the short-time A-line profiles may include the steps of: obtaining, by the image processor, the interference intensities corresponding to each wave number for a specific point on the measurement target from the selected interference images; and obtaining, by the image processor, the short-time A-line profiles corresponding to each wave number domain by performing short-time Fourier transform on the obtained interference intensities in the wave number domains.

According to an embodiment, the method may further include the steps of: creating, by the image processor, a depth-directional movement function corresponding to depth-directional movement of the measurement target; creating, by the image processor, a phase compensation function corresponding to the depth-directional movement by integrating the depth-directional movement function; extracting, by the image processor, interference intensities at each identical point in the plurality of interference images; and compensating, by the image processor, for phases of interference signals indicating distribution of the extracted interference intensities in the wave number domain for each identical point based on the phase compensation function.

A computer-readable storage medium according to an embodiment of the present disclosure may store a program including commands for performing each step of the method of determining depth-directional movement of a measurement target and compensating for the depth-directional movement of the measurement target in a full-field OCT system.

According to an embodiment of the full-field OCT system of the present disclosure, when the depth-directional movement and the horizontal movement of the measurement target can be measured, the depth-directional movement and the horizontal movement can be measured simultaneously.

According to an embodiment of the full-field OCT system of the present disclosure, it is possible to compensate for the depth-directional movement and the horizontal movement of the measurement target in an OCT image.

According to an embodiment of the full-field OCT system of the present disclosure, it is possible to quickly compensate for movement of the measurement target in an OCT image by simplifying an algorithm for measuring and compensating for the depth-directional movement and the horizontal movement of the measurement target.

DETAILED DESCRIPTION

Figure 1:
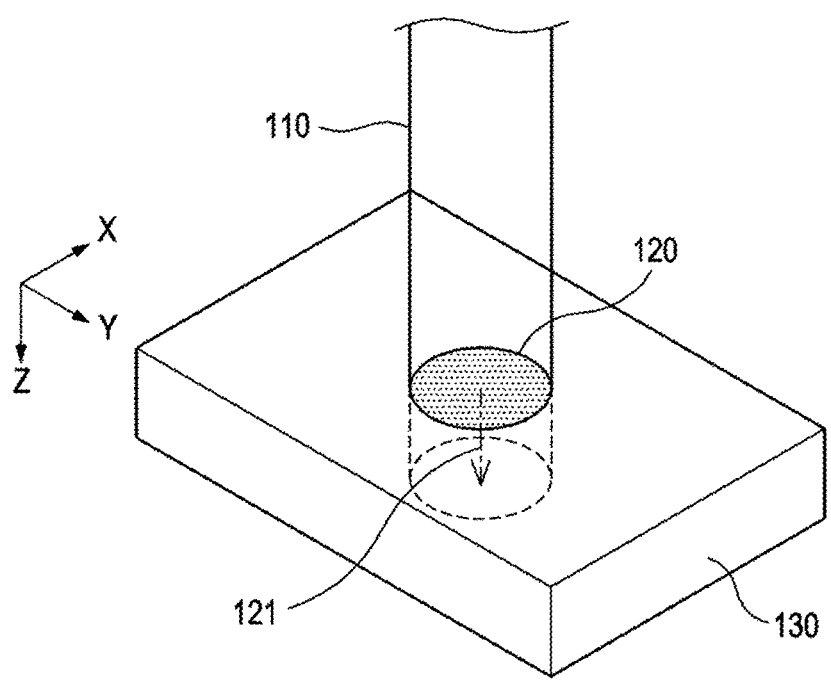
FIG. 1 is a drawing illustrating an OCT measurement method and the influence by movement of a measurement target in a full-field OCT system.

Embodiments stated herein are provided as examples for describing the present disclosure. The embodiments may be realized in various ways and the present disclosure should not be construed as being limited to the embodiments and the detailed description of the embodiments presented below.

The term "unit' used herein means software and a hardware component such as a Field-Programmable Gate Array (FPGA) and an Application Specific Integrated Circuit (ASIC). However, the "unit" is not limited to hardware and software. The "unit" may be configured to be stored on a storage medium that can be addressed or may be configured to operate one or more processors. Accordingly, for example, the "unit" includes components such as software components, object-oriented software components, class components, and task components, a processor, a function, a property, a procedure, a subroutine, the segment of a program code, a driver, a firmware, a microcode, a circuit, data, a database, a data structure, a table, an array, and a variable. Functions provided by the components and the "unit" may be combined in a smaller number of components and "unit", or may be further separated into additional components and "units".

Unless otherwise defined, all terms including technical and scientific terms used in the following description have the same meaning as commonly understood by those skilled in the art to which this disclosure pertains. All terms used herein are chosen not to limit the scope of the present disclosure, but to describe the present disclosure more clearly.

Expressions in the singular form described herein may include the expression in the plural form unless stated otherwise, and the same applies for expressions in the singular form recited in claims.

Terms such as 'first', 'second', etc. stated in various embodiments described herein are used only for the purpose of distinguishing a plurality of elements from other elements, rather than to limit the order or priority of the elements.

The terms "comprise", "include", "have", etc. used herein should be understood as open-ended terms implying the possibility of including other embodiments, unless stated otherwise in phrases and sentences including such terms.

The expressions 'based on' and 'on the basis of' used herein are used to describe one or more factors influencing decisions, determinations, or operations stated in phrases or sentences including such expressions, without excluding additional factors influencing such decisions, determinations, or operations.

It will be understood that when an element is referred to as being "coupled" or "connected" to another element, it can be directly coupled or connected to the other element or intervening elements may be present between the element and another element.

Hereafter, embodiments of the disclosure are described with reference to the accompanying drawings. The same reference numerals are given to the same elements in the drawings and repetitive descriptions of the same element may be omitted.

A full-field OCT system can create an OCT image, using a plurality of interference images formed by interference between reference light, that is created when a laser beam having a predetermined scanning area is reflected by a reference mirror, and reflective light that is created when the laser beam is reflected by a measurement target.

FIG. 1 is a drawing illustrating an OCT image measurement method and an influence by movement of a measurement target in a full-field OCT system. As illustrated in FIG. 1, the full-field OCT system can capture interference images that are created for a measurement region corresponding to an irradiation area 120 on the measurement target 130 by interference between reflective light, that is formed when a laser beam 110 having a fixed irradiation area 120 is reflected by the measurement target 130, and reference light that is formed when the same laser beam 110 is reflected by a reference mirror. The full-field OCT system can obtain information in a depth direction 121 of the measurement target 130 by extracting interference signals for the measurement region from the captured interference images and can create an OCT image based on the obtained information.

However, if the measurement target 130 moves while the full-field OCT system captures the interference images, the interference signals are easily influenced by the movement of the measurement target 130. Further, an OCT image created using the interference signals reflecting the movement of the measurement target 130 may include artifacts resulting from the movement of the measurement target 130. For example, if the measurement target 130 moves in the depth direction 121 while the full-field OCT system captures interference images, the created OCT image may include artifacts resulting from the movement of the measurement target 130 in the depth direction 121.

Figure 2:
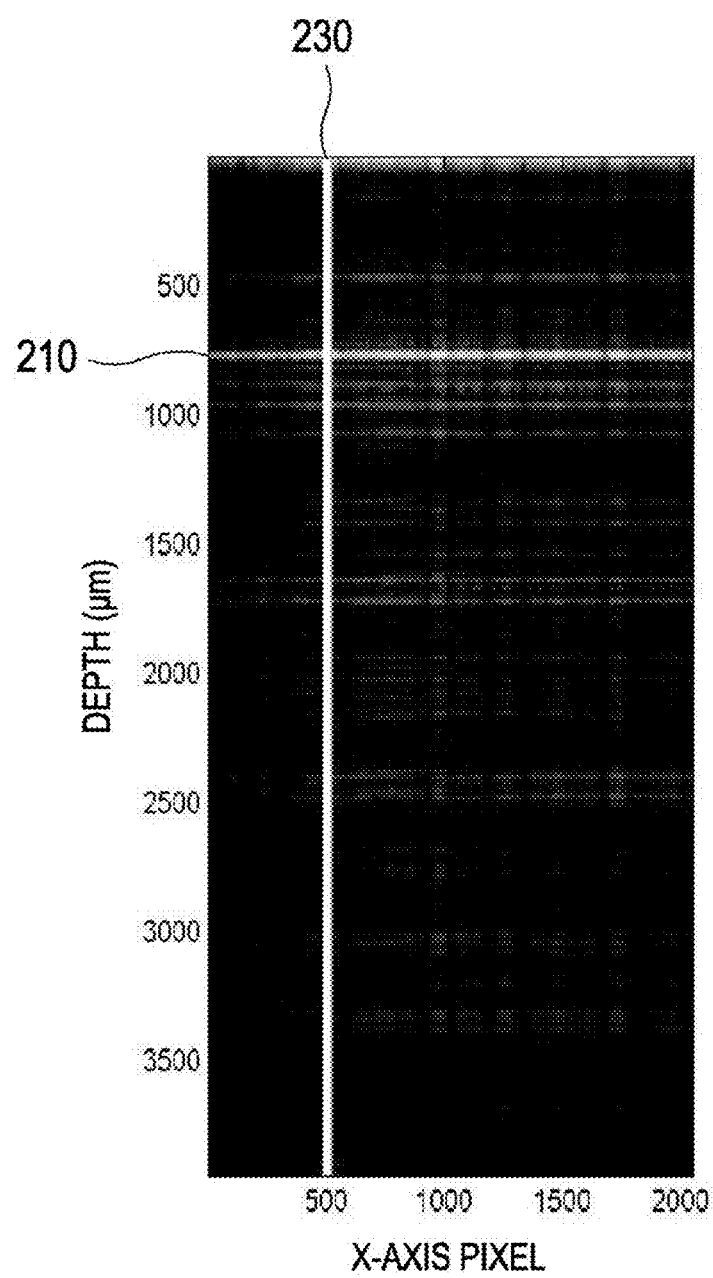
FIG. 2 is a two-dimensional OCT image created when there is no depth-directional movement of a mirror that is the measurement target in a full-field OCT system.
Figure 3:
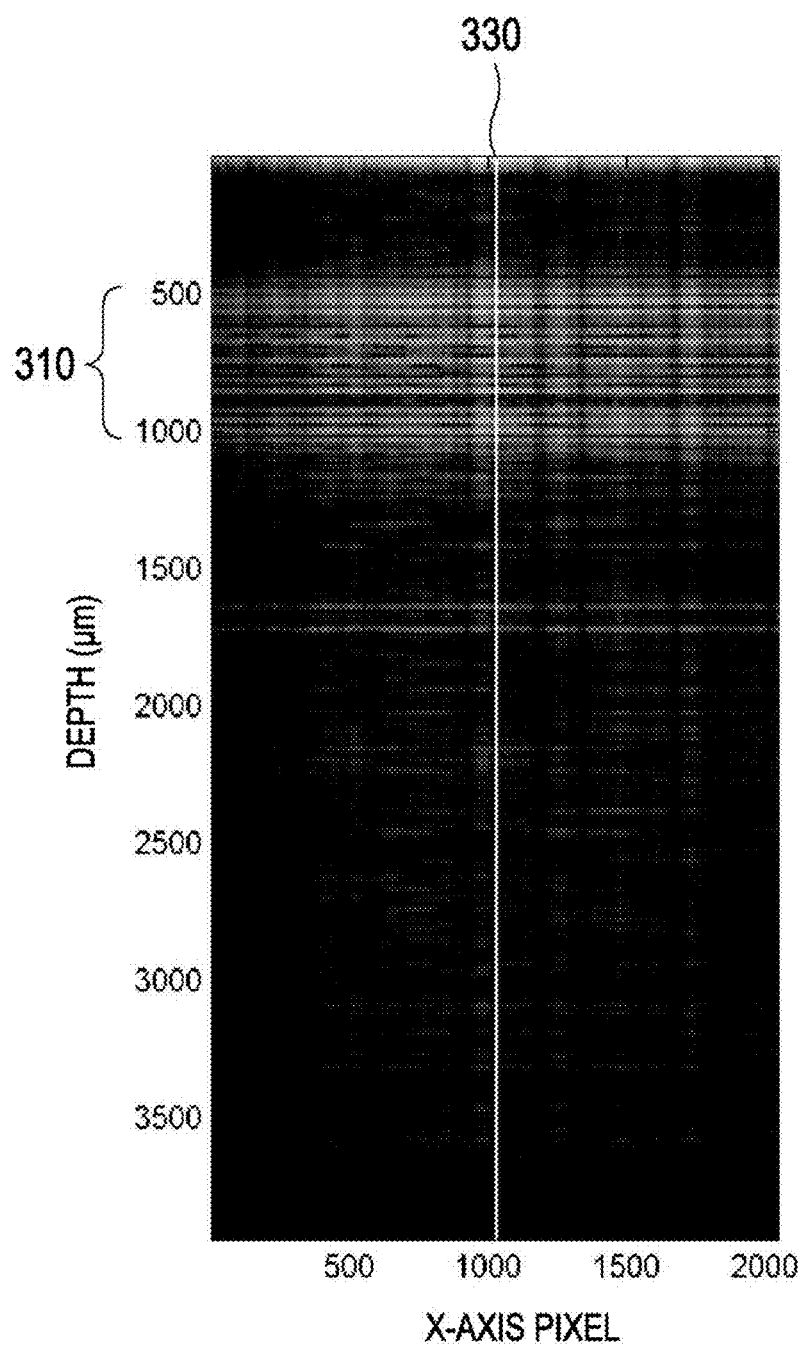
FIG. 3 is a two-dimensional OCT image created when there is a depth-directional movement of a mirror that is the measurement target in a full-field OCT system.

FIGS. 2 and 3 are a 2D OCT image created when there is no depth-direction movement of a mirror that is the measurement target and a 2D OCT image created when there is a depth-directional movement of the mirror that is the measurement target in a full-field OCT system. The illustrated 2D OCT images are OCT cross-sectional images showing x-axis and z-axis (axis in depth direction) cross-sections of the measurement target. The full-field OCT system can create a 3D (three-dimensional) OCT image by combining a plurality of OCT cross-sectional images created in y-axis direction (that is, OCT cross-sectional images showing the x-axis and z-axis cross-sections) of the measurement target.

As illustrated in FIG. 2, when there is no depth-directional movement of the mirror that is the measurement target, the shape 210 of the mirror may be shown as a horizontal line in the 2D OCT image. However, as illustrated in FIG. 3, when there is depth-directional movement of the mirror, artifacts due to the depth-directional movement may appear in the form of an after-image 310 in the 2D OCT image. In this case, the shape of the mirror may not be clearly shown in the 2D OCT image.

According to the present disclosure, it is possible to measure the depth-directional movement of a measurement target by observing a peak of a short-time A-line (Axial-line) profile corresponding to a point in time where interference images of the measurement target are captured. Here, the "short-time A-line profile" may mean, in an OCT system or a full-field OCT system, a result of short-time Fourier transform on interference intensities in a wave number domain, in which the interference intensities are obtained from a point corresponding to a specific point on a measurement target in interference images included in the wave number domain corresponding to the wavelength domain of a laser converted for a short time among interference images captured from the measurement target in accordance with embodiments to be described below. Accordingly, an OCT image where the depth-directional movement has been compensated for can be created by correcting phases of the interference signals based on the measured depth-directional movement.

Further, in the present disclosure, horizontal movement of a measurement target can be measured based on the cross-correlation of interference images of the measurement target. Accordingly, an OCT image where the horizontal movement has been compensated for can be created by performing image registration between interference images based on the measured horizontal movement.

A method of measuring depth-directional and horizontal movement of a measurement target in a full-field OCT system according to various embodiments of the present disclosure, particularly the full-field OCT system using a wavelength-tunable laser, and of compensating for the measured depth-directional movement and horizontal movement of the measurement target in an OCT image is described in detail hereafter.

<Measurement and Compensation of Depth-Directional Movement>

Figure 4:
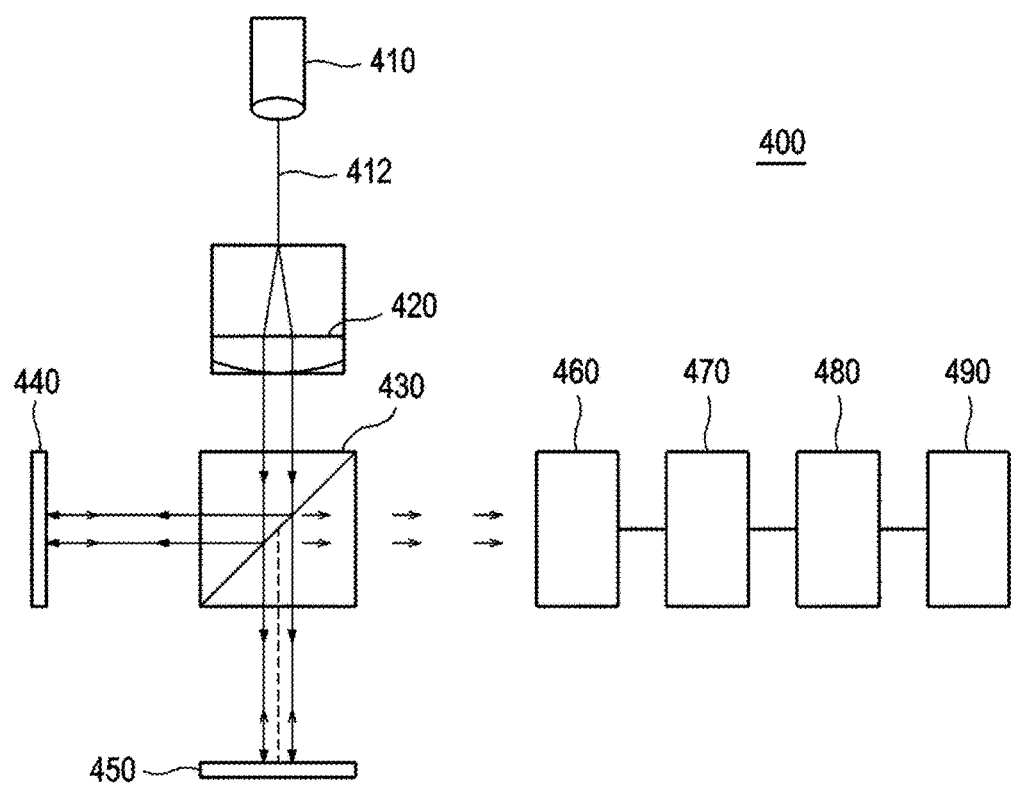
FIG. 4 is a block diagram illustrating the configuration of a full-field OCT system according to an embodiment of the present disclosure.

FIG. 4 is a block diagram illustrating a configuration of a full-field OCT system 400 according to an embodiment of the present disclosure. As illustrated in the figure, the full-field OCT system 400 may include a wavelength-tunable laser 410, a lens 420, a beam splitter 430, a reference mirror 440, an imaging device 460, a storage unit 470, and an image processor 480. According to an embodiment, the full-field OCT system 400 can create an OCT image using interference images created by an interferometer realized using the wavelength-tunable laser 410, the beam splitter 430, the reference mirror 440, the imaging device 460 etc. The configuration of the interferometer of the full-field OCT system 400 is not limited to these components and the connection relation among the components, and the components and the connection relation can be changed in various ways as long as the interferometer can effectively create the same interference images.

The wavelength-tunable laser 410 may be a laser that can radiate a laser beam having wavelengths corresponding to each wave number by tuning a wavelength. A part of the laser beam radiated from the wavelength-tunable laser 410 can become the reference light by being reflected by the reference mirror 440. The other part of the laser beam radiated from the wavelength-tunable laser 410 is irradiated to the measurement target 450 and can become the reflective light by being reflected by the measurement target 450.

According to an embodiment, when the laser beam is irradiated to the lens 420 from the wavelength-tunable laser 410, the lens 420 refracts the incident laser beam, so that a laser beam having a predetermined irradiation area can be emitted. According to an embodiment, the wavelength-tunable laser 410 and the lens 420 can be connected to each other through an optical fiber 412. According to another embodiment, the laser beam from the wavelength-tunable laser 410 can travel directly to the lens 420 through a free space or the atmosphere.

A part of the laser beam refracted by the lens 420 can be irradiated to the measurement target 450 through the beam splitter 430. The other part of the laser beam refracted by the lens 420 can be reflected at the beam splitter 430 and irradiated toward the reference mirror 440. The beam splitter 430 can, while transmitting the laser beam, which is reflected from the reference mirror 440 (i.e., the reference light), to the imaging device 460 by passing the laser beam, transmit the laser beam, which is reflected from the measurement target 450 (i.e., the reflective light), to the imaging device 460 by reflecting the laser beam.

The imaging device 460 can make an interference image that is formed by interference between the reference light and the reflective light by receiving the reflective light and the reference light from the beam splitter 430. According to an embodiment, the imaging device 460 can create an interference image at each point in time where the wavelength of the wavelength-tunable laser 410 is sequentially changed. Accordingly, the full-field OCT system 400 can sequentially make and create a plurality of interference images through the imaging device 460 included in the interferometer while sweeping the wavelength of the wavelength-tunable laser 410. According to an embodiment, the imaging device 460 may be implemented using a camera or a video camera, but is not limited thereto.

Figure 5:
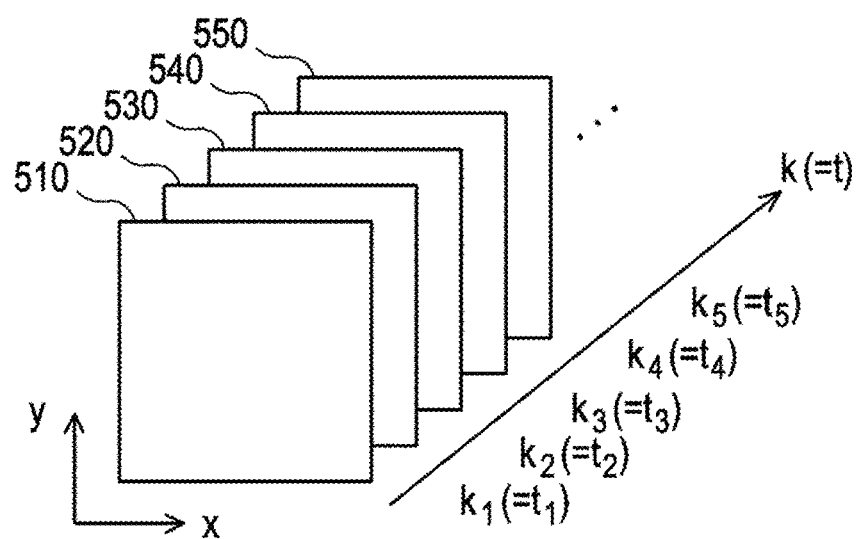
FIG. 5 is a diagram illustrating a plurality of interference images captured while the wavelength of the wavelength-tunable laser is sequentially changed in the full-field OCT system according to an embodiment of the present disclosure.

FIG. 5 is a diagram illustrating a plurality of interference images 510, 520, 530, 540, and 550 captured while the wavelength of the wavelength-tunable laser 410 is sequentially changed in the full-field OCT system 400 according to an embodiment of the present disclosure. For example, the interference images 510, 520, 530, 540, and 550 may be created by the imaging device 460 at each point in time t1, t2, t3, t4, and t5 where the wavelength of the wavelength-tunable laser 410 is changed to λ1, λ2, λ3, λ4, and 2δ. The point in time where the wavelength is changed from λ1 to λ5 may be defined by the wave number. That is, as illustrated in FIG. 5, λ1, λ2, λ3, λ4, and λ5 may correspond to k1, k2, k3, k4, and k5, respectively, and the wave number k1, k2, k3, k4, and k5 may represent the point in time where the wavelength is changed from λ1 to λ5. The transformation relationship between the wave number kn and the wavelength % n can be defined by the following equation.

$$k_n = \frac{2\pi}{\lambda_n}$$

With reference to FIG. 4, the storage unit 470 can receive and store a plurality of interference images created by the imaging device 460. According to an embodiment, the storage unit 470 may be implemented using at least one volatile memory device or nonvolatile memory device, or a combination of such memory devices. In detail, the storage unit 470 may be implemented using a volatile memory device such as a DRAM, SRAM etc., or a nonvolatile memory device such as a flash memory, a hard disk, an MRAM, a PRAM etc., or a combination of these memory devices.

The image processor 480 can create an OCT image of the measurement target 450, using the interference images stored on the storage unit 470. Further, the image processor 480 can determine and compensate for depth-directional movement of the measurement target 450 based on the interference images stored on the storage unit 470. In the embodiment illustrated in FIG. 4, the full-field OCT system 400 includes the storage unit 470 between the imaging device 460 and the image processor 480, however in another embodiment, the full-field OCT system 400 may omit the storage unit 470, and the image processor 480 may receive interference images directly from the imaging device 460.

According to an embodiment, the full-field OCT system 400 may further include a display 490 that can display depth-directional movement of the measurement target 450 or an OCT image where the depth-directional movement has been compensated. The display 490 can receive and display information about the OCT image or the depth-directional movement of the measurement target 450 from the image processor 480.

Hereinafter, a method of determining depth-directional movement of the measurement target 450 by the image processor 480 is described in detail.

First, while sweeping the wavelength of the wavelength-tunable laser 410, the interferometer can sequentially create a plurality of interference images. The plurality of interference images created by the interferometer can be stored on the storage unit 470 or transferred directly to the image processor 480.

The image processor 480 can obtain interference intensities corresponding to each wave number included in each wave number domain for a specific point on the measurement target 450 from interference images corresponding to each wave number included in each wave number domain among the plurality of interference images. In detail, the image processor 480 can extract interference images corresponding to each wave number included in each sliding wave number domain window from the plurality of interference images by sequentially applying the sliding wave number domain window having predetermined sizes to the plurality of interference images. The image processor 480 can obtain interference intensities corresponding to each wave number included in each wave number domain for the specific point on the measurement target 450 from the obtained interference images corresponding to each wave number included in each wave number domain.

Figure 6:
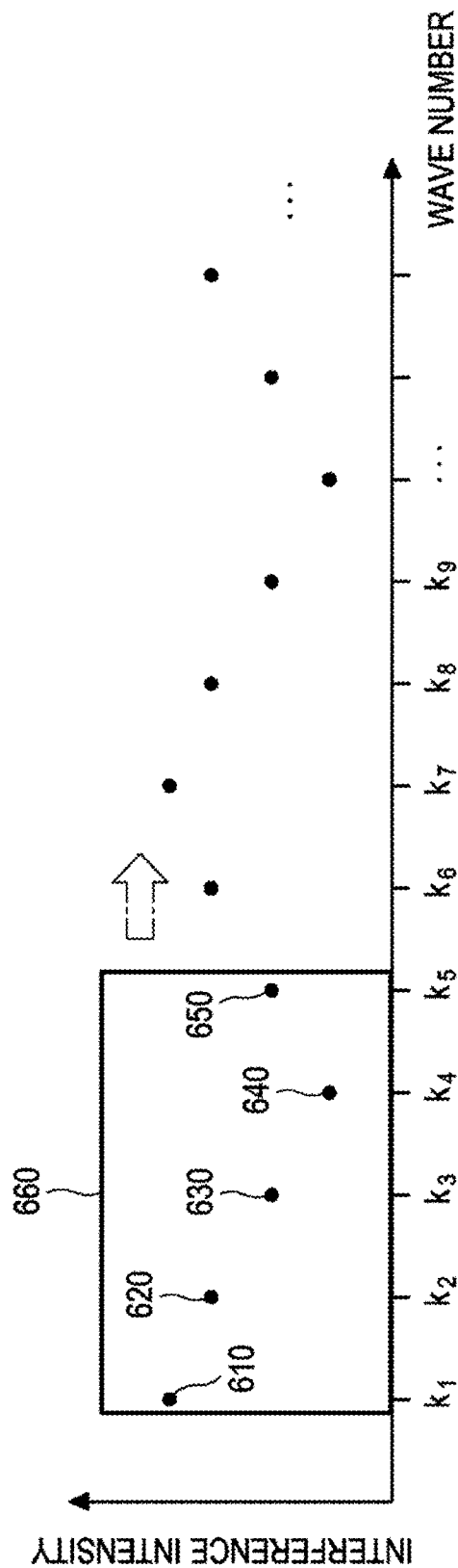
FIG. 6 is a drawing showing a process of obtaining a short-time wave number domain profile by applying a sliding wave number domain window to interference images in the full-field OCT system according to an embodiment of the present disclosure.

FIG. 6 is a drawing showing a process of obtaining a short-time wave number domain profile by applying a sliding wave number domain window to interference images in the full-field OCT system 400 according to an embodiment of the present disclosure. Here, the "short-time wave number domain profile" may mean a change in interference intensity according to a change in wave number corresponding to a wave length change for a short time period. With reference to FIGS. 5 and 6, the image processor 480 can sequentially obtain the interference intensities for the short time period while a wave length is changed four times by applying the sliding wave number domain window 660 having a size 5 in a wave number domain for the plurality of interference images. That is, as the sliding wave number domain window 660 is moved in the wave number domain, the interference intensities can be obtained from the interference images corresponding to each wave number included in the size of the sliding wave number domain window 660. For example, as illustrated in the figures, when the sliding wave number domain window 660 is applied to a wave number domain of k1 to k5, the image processor 480 can obtain interference intensities 610, 620, 630, 640, and 650 from interference images 510, 520, 530, 540, and 550 captured for a short time period while the wave number changes from k1 to k5. Thereafter, the image processor 480 can obtain interference intensities by applying the sliding wave number domain window 660 to the next wave number domain, that is, a wave number domain of k2 to k6 in accordance with a sequence where the wavelength of the wavelength-tunable laser 410 is changed.

Figure 7:
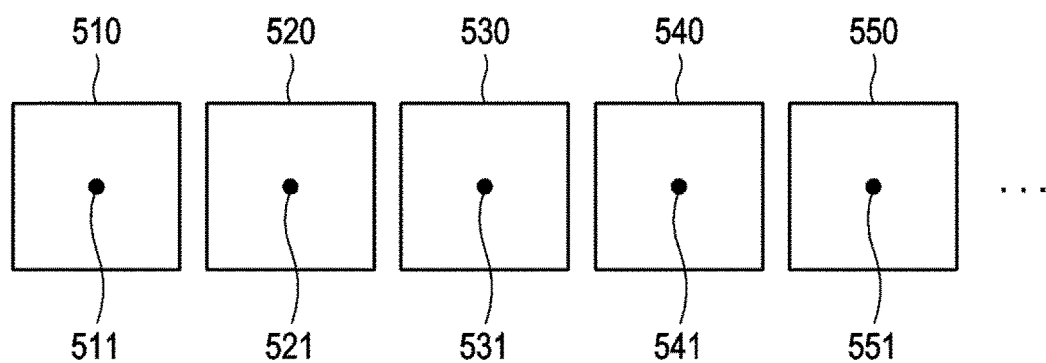
FIG. 7 is a drawing showing a process of obtaining interference intensities from identical points in each of the plurality of interference images in the full-field OCT system according to an embodiment of the present disclosure.

In this case, the interference intensities can be obtained at identical points corresponding to the specific point on the measurement target 450 in the interference images. For example, as illustrated in FIG. 7, when the image processor 480 applies the sliding wave number domain window 660 to the wave number domain of k1 to k5, interference intensities can be obtained from identical points 511, 521, 531, 541, 551 corresponding to the specific point on the measurement target 450 in the interference images 510, 520, 530, 540, and 550 captured in the wave number domain.

As described above, when interference intensities in short-time wave number domains are obtained by sequentially applying a sliding wave number domain window to a plurality of interference images, the image processor 480 can obtain a plurality of short-time A-line profiles corresponding to each short-time wave number domain based on the interference intensities in each wave number domain. In detail, first, the image processor 480 can obtain short-time wave number domain profiles for short-time interference intensities obtained by applying each sliding wave number domain window. Further, the image processor 480 can obtain a plurality of short-time A-line profiles by performing short-time Fourier transform in the wave number domain for each obtained short-time wave number domain profile.

For example, with reference to FIG. 6, when the sliding wave number domain window 660 is applied to the wave number domain of k1 to k5, the image processor 480 can obtain the short-time wave number domain profile showing a wave number domain distribution of the interference intensities 610, 620, 630, 640, and 650 in the short-time wave number domain. The image processor 480 can obtain a short-time A-line profile from the short-time wave number domain profile by performing short-time Fourier transform on the wave number of the short-time wave number domain profile. In the same manner, the image processor 480 can obtain each short-time wave number domain profile for the interference intensities in obtained other short-time wave number domains by sequentially applying the sliding wave number domain window 660, and can obtain short-time A-line profiles by performing short-time Fourier transform on the wave numbers of the obtained short-time wave number domain profiles.

Figure 8:
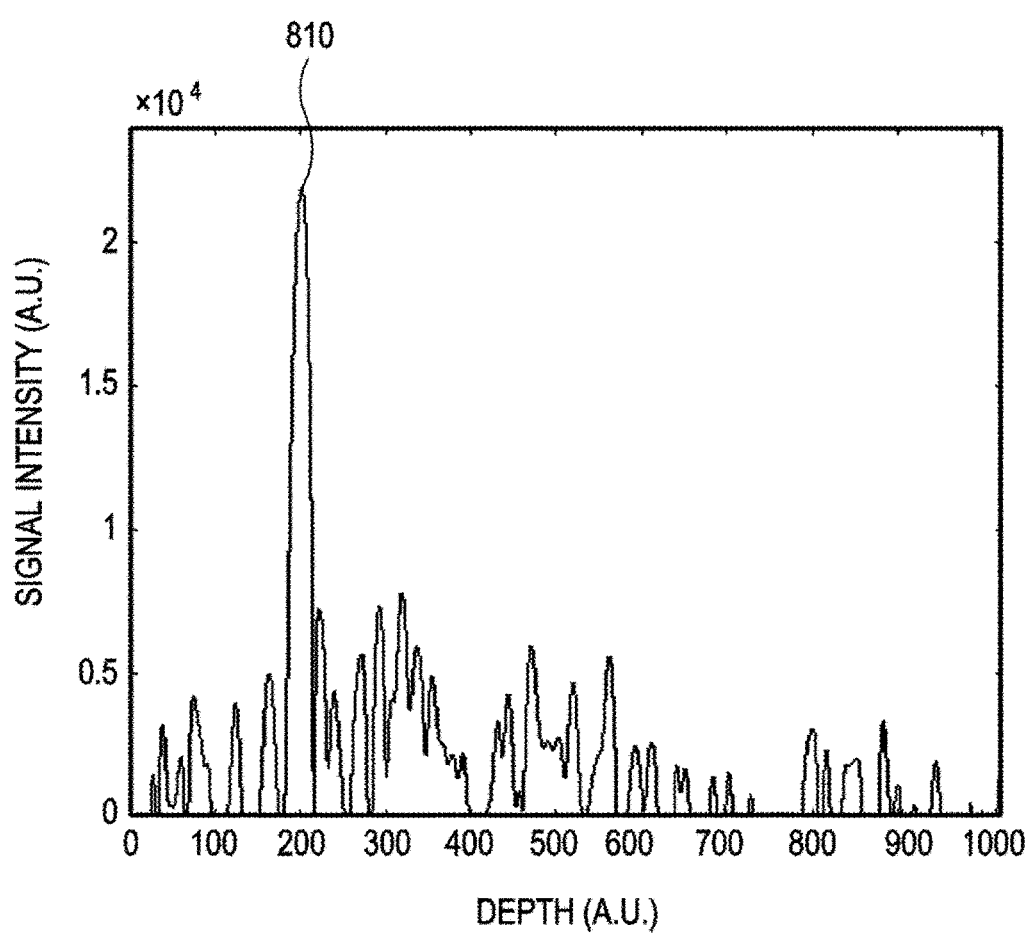
FIG. 8 is a drawing showing a short-time A-line profile obtained by performing short-time Fourier transform on the wave number of a short-time wave number domain profile in the full-field OCT system according to an embodiment of the present disclosure.

FIG. 8 shows an example of a short-time A-line profile obtained by performing short-time Fourier transform on a wave number for a short-time wave number domain profile in the full-field OCT system 400 according to an embodiment of the present disclosure. When the short-time Fourier transform is performed on the wave number for the short-time wave number domain profile, the image processor 480 can obtain intensity (vertical axis) information of the short-time wave number domain profile according to the depth (horizontal axis) at a specific point on the measurement target 450. The "A.U." shown at the horizontal axis of the short-time A-line profile graph in FIG. 8 is an abbreviation of arbitrary unit. The "A.U." indicated in other drawings has the same meaning.

The image processor 480 can determine depth-directional movement of the measurement target 450 by observing depth values in short-time A-line profiles. In detail, the image processor 480 can obtain the depth values corresponding to each peak of the short-time A-line profiles that correspond to each short-time wave number domain profile obtained by sequentially applying the sliding wave number domain window. The image processor 480 can determine depth-directional movement of the measurement target 450 based on changes of the wave numbers of the obtained depth values. In this case, since each wave number may correspond to each point in time when the wavelength of the wavelength-tunable laser 410 is changed, the changes of the wave numbers may correspond to lapse of time or change of time while the wavelength of the wavelength-tunable laser 410 is changed. Accordingly, the change of the wave numbers for the depth values may mean the change over time of the depth values while the wavelength of the wavelength-tunable laser 410 is changed.

Figure 9:
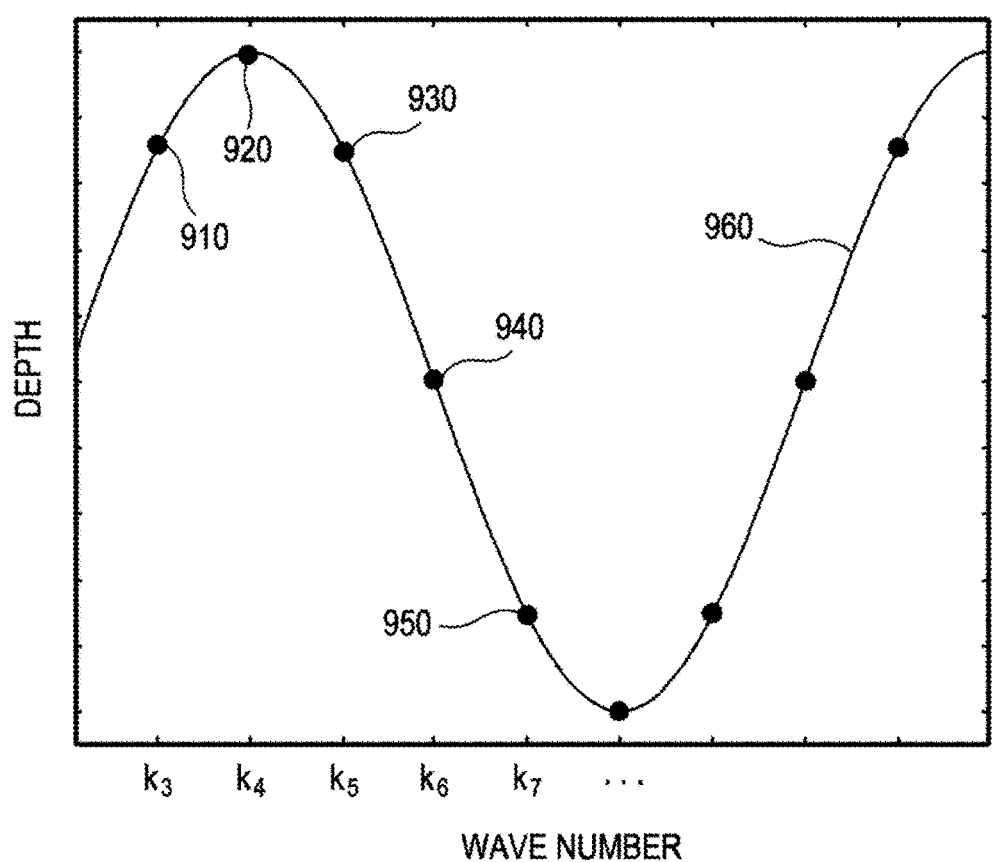
FIG. 9 is a spectrogram showing depth-directional movement at a specific point of the measurement target obtained in the full-field OCT system according to an embodiment of the present disclosure.

FIG. 9 shows an example of a spectrogram showing depth-directional movement at a specific point on the measurement target 450 obtained by the full-field OCT system 400 according to an embodiment of the present disclosure. The spectrogram can be expressed by the distribution of depth values (vertical axis) according to the wave number (horizontal axis). With reference to FIGS. 6 and 8, the image processor 480 can obtain the short-time A-line profile as illustrated in FIG. 8 based on the interference intensities 610, 620, 630, 640, and 650 obtained from the sliding wave number domain window 660 of the wave number domain from k1 to k5. The image processor 480 can obtain a depth value 910 corresponding to a peak 810 of the obtained short-time A-line profile. In this case, the obtained depth value 910 may be determined as a representative value included in the wave number domain applied for obtaining the short-time A-line profile, for example, a depth value 910 for an average value or a median value. For example, the depth value 910 obtained from the wave number domain of k1 to k5 may be determined as a depth value 910 for k3 that is the median value.

Then, the image processor 480 can obtain the short-time A-line profiles based on the interference intensities obtained by moving the sliding wave number domain window 660. In the same manner, the image processor 480 can obtain depth values 920, 930, 940, and 950 of the measurement target 450 corresponding to each of k4, k5, k6, k7 that are the next points in time where the wave length is changed, by obtaining depth values corresponding to each peak of the obtained short-time A-line profiles. As illustrated in FIG. 9, the image processor 480 can determine depth-directional movement of the measurement target 450 while sweeping the wavelength of the wavelength-tunable laser 410 by observing the depth values 910, 920, 930, 940, and 950 of the measurement target 450 corresponding to each point in time k3, k4, k5, k6, and k7 where the wavelength is changed.

When the depth-directional movement of the measurement target 450 is determined, the image processor 480 can display the depth-directional movement of the measurement target 450 to a user while capturing an OCT image. Further, the image processor 480 can compensate for the influence of the depth-directional movement in the OCT image based on the depth-directional movement of the measurement target 450.

According to an embodiment, the image processor 480 can store all interference images created by the interferometer on the storage unit 470 in advance, determine depth-directional movement of the measurement target 450 using the interference images, and display the depth-directional movement through the display 490. According to another embodiment, every time an interference image is created by the interferometer, the image processor 480 can receive the interference images, determine depth-directional movement of the measurement target 450, and display the depth-directional movement through the display 490 in real time.

Figure 10:
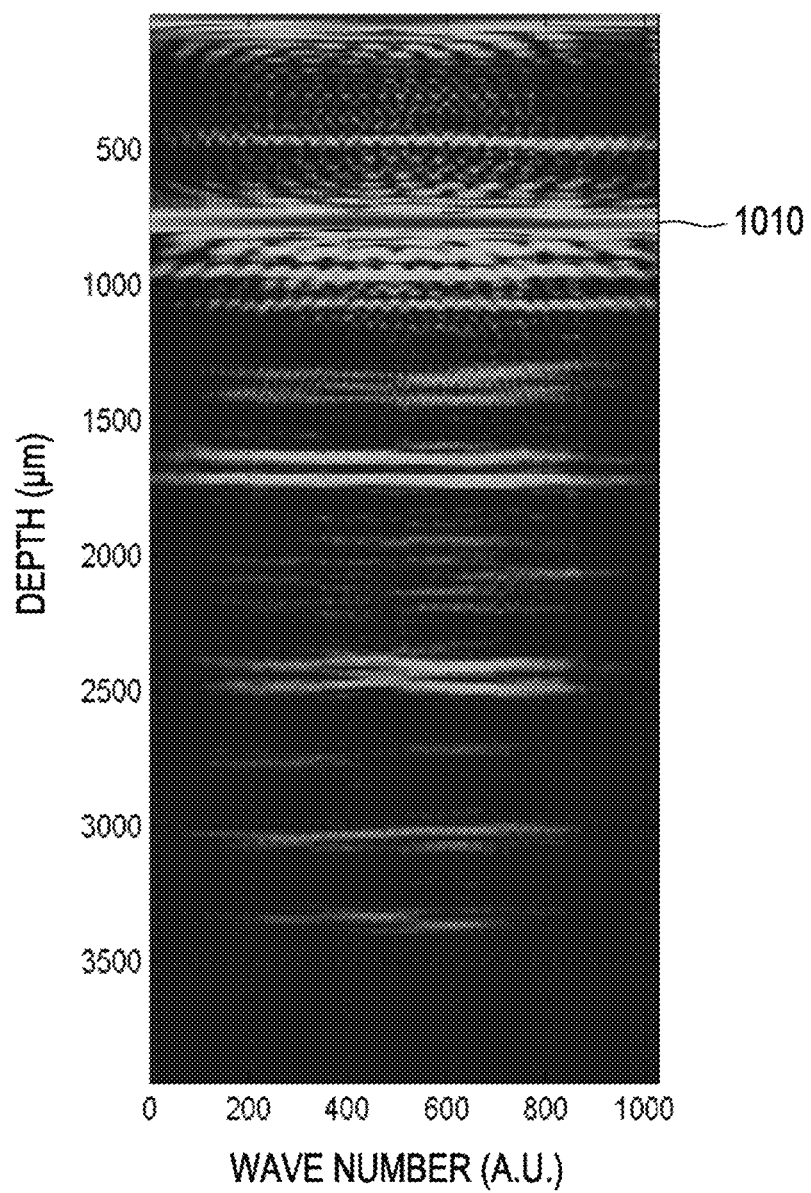
FIG. 10 is a spectrogram showing depth-directional movement of a measurement target obtained when a mirror that is the measurement target does not move in the depth direction in the full-field OCT system according to an embodiment of the present disclosure.
Figure 11:
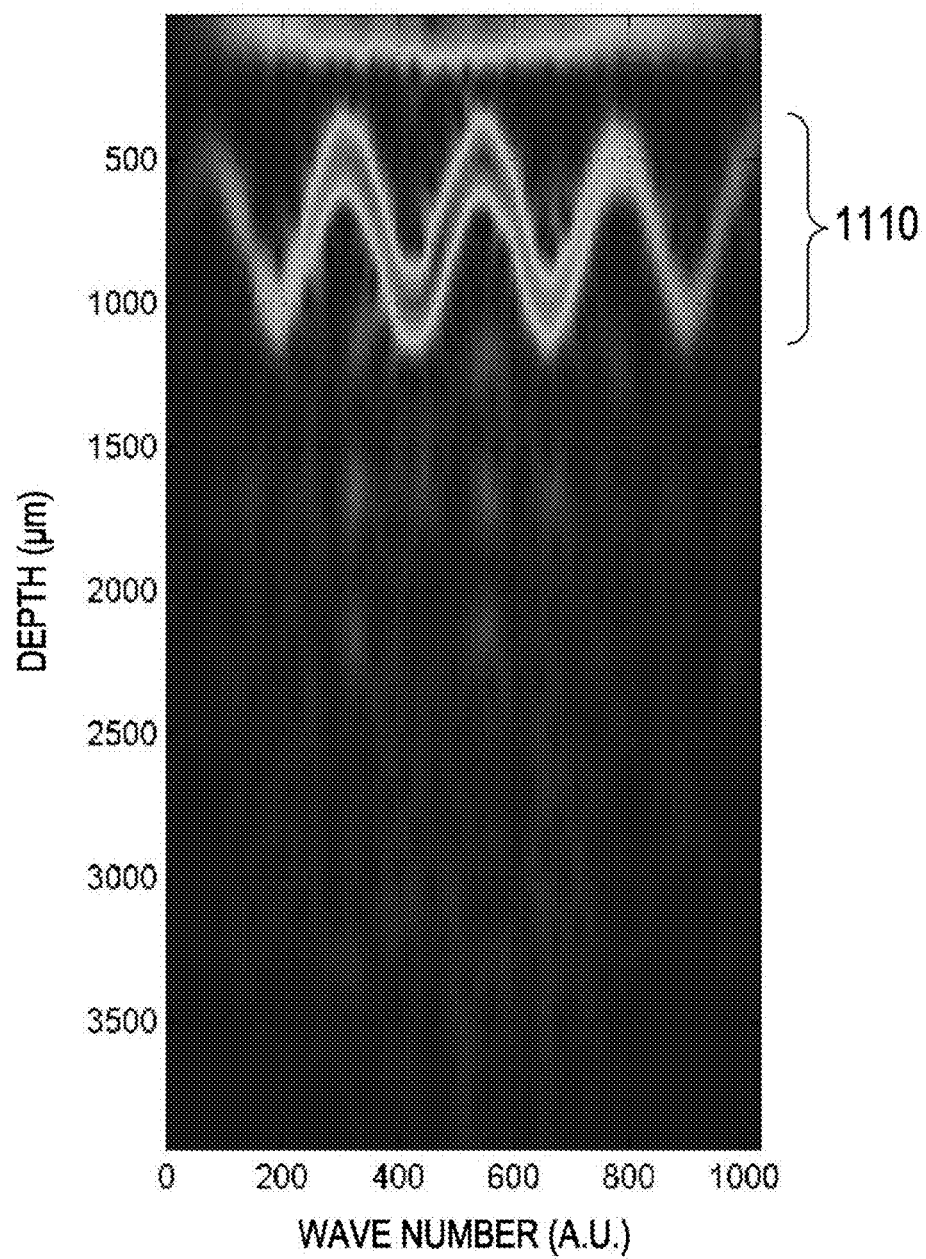
FIG. 11 is a spectrogram showing depth-directional movement of a measurement target obtained when a mirror that is the measurement target moves in the depth direction in the full-field OCT system according to an embodiment of the present disclosure.

FIGS. 10 and 11 are spectrograms showing the depth-directional movement of a measurement target obtained when the mirror that is the measurement target is not moved in the depth direction and when the mirror that is the measurement target is moved in the depth direction in the full-field OCT system according to an embodiment of the present disclosure. In detail, with reference to FIGS. 2 and 3, FIG. 10 is a spectrogram showing depth-directional movement measured based on one point 230 on the mirror when the mirror is not moved in the depth direction as illustrated in FIG. 2. Since there is no depth-directional movement, a depth-directional position 1010 of the peak of the A-line profile is not changed at each point in time where the wavelength of the wavelength-tunable laser expressed as a wave number is changed. Meanwhile, the white lines under the position 1010 in FIG. 10 are artifacts created by interference between reflective lights that are created when the laser beam is reflected by optical parts used in the full-field OCT system 400.

FIG. 11 is a spectrogram showing depth-directional movement measured based on one point 330 of the mirror when the mirror is moved in the depth direction of the mirror as illustrated in FIG. 3. Since there is depth-directional movement, the depth-directional position of the peak of the A-line profile is changed in accordance with depth-directional movement at each point in time where the wavelength of the wavelength-tunable laser is changed.

When the depth-directional movement of the measurement target 450 is determined through this process, the image processor 480 can compensate for the influence of the depth-directional movement for a phase of an interference signal in an OCT image based on the depth-directional movement. To that end, the image processor 480 can create a depth-directional movement function corresponding to the depth-directional movement of the measurement target 450 and then can create a phase compensation function corresponding to the depth-directional movement of the measurement target 450 by integrating the depth-directional movement function. Then, the image processor 480 can compensate for the depth-directional movement of the measurement target 450 by compensating for the phases of interference images for creating the OCT image based on the phase compensation function.

In detail, with reference to FIG. 9, the image processor 480 can create a depth-directional movement function 960 by performing curve fitting on a change of the depth value (e.g. changes of the depth value to 910, 920, 930, 940, and 950) of the peak of the A-line profile according to a change in the wave number (e.g. changes of the wave number to k3 to k4, k5, k6, and k7), in which the changes of the depth value correspond to the depth-directional movement of the measurement target 450 at each point in time where the wavelength is changed. For example, a reference function for performing curve fitting may be defined as follows.

$$a0 + a1 \cdot \cos(w1 \cdot k) + a2 \cdot \sin(w1 \cdot k)$$

(where, a0 is a constant, a1 is the magnitude of the cosine function, a2 is the magnitude of sine function, w1 is the frequency of the cosine function and of the sine function, and k is a wave number)

The image processor 480 can determine values of variables a0, a1, a2, and w1 of the reference function by performing curve fitting using the reference function on a change of the depth value of the peak of the A-line profile according to a change of the wave number. The image processor 480 can create the depth-directional movement function 960 corresponding to depth-directional movement of the measurement target 450 by applying the determined values of the variables to the reference function.

Curve fitting may be performed, for example, by appropriately selecting one algorithm from curve fitting algorithms such as regression analysis, linear interpolation, or spline interpolation. Further, one of the functions that can express movement of the measurement target 450 well, including a trigonometric function, a polynomial function, a B-spline curve etc. may be selected for the reference function.

The phase compensation function can be created by integrating the created depth-directional movement function over an integral interval that is the wave number domain corresponding to the entire period where the wavelength of the wavelength-tunable laser 410 is changed. When there is depth-directional movement of the measurement target 450, the phases of the interference signals that are used to create an OCT image may be distorted by the depth-directional movement. The phase compensation function can show the degree of distortion of phases due to depth-directional movement of the measurement target 450 at each point in time where the wavelength is changed. Accordingly, the image processor 480 can create an OCT image where the influence of the depth-directional movement has been compensated, by compensating for the phases of the interference signals based on the phase compensation function.

For example, it may be assumed that an interference signal before the phase distortion is compensated is I(k) and an interference signal after the phase distortion is compensated is Icomp(k). Here, the interference signal may be defined as a signal that indicates the wave number domain distribution of interference intensities obtained at points corresponding to any one point on the measurement target 450, in interference images. When the phase compensation function is θ(k), the phase distortion of an interference signal can be compensated through the following equation.

$$I\text{comp}(k) = I(k) \cdot e^{-i\theta(k)}$$

(where k is the wave number)

The image processor 480 can compensate for the phase distortion of the interference signal at a point corresponding to one point of the measurement target 450 in an interference image through the equation above. Accordingly, the image processor 480 can create an OCT image where the influence due to depth-directional movement has been completely compensated, by obtaining all interference signals for the measurement domain of the measurement target 450 by extracting interference intensities at each identical point in a plurality of interference images, and then by compensating phase distortion of all interference signals in the same manner. The image processor 480 can create a phase compensation function for each point on the measurement target 450 and compensate for the depth-directional movement at each point on the measurement target 450 using each phase compensation function corresponding to each point on the measurement target 450.

Figure 12:
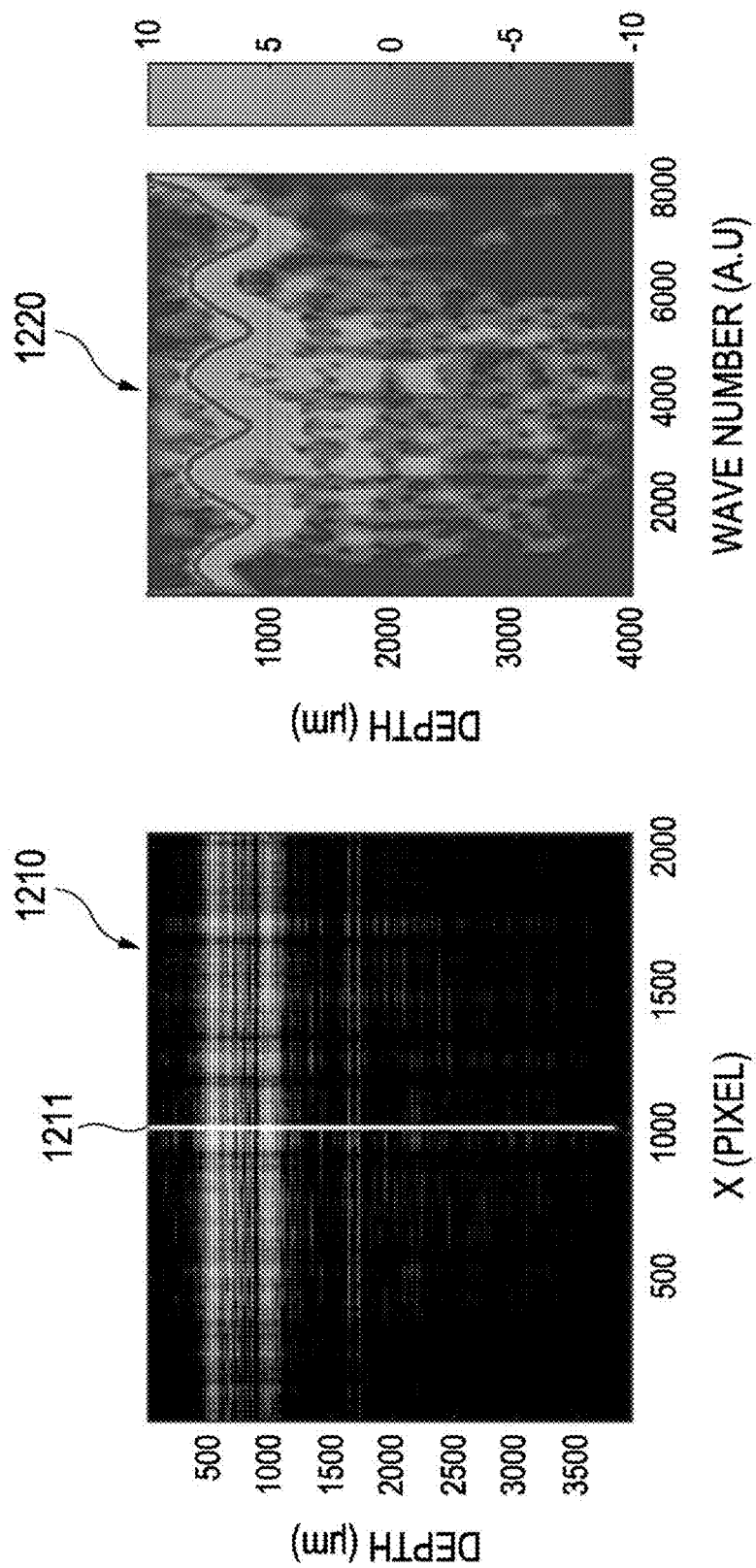
FIG. 12 shows a two-dimensional OCT image and a spectrogram before depth-directional movement of the mirror that is the measurement target is compensated for in the full-field OCT system according to an embodiment of the present disclosure.

FIG. 12 shows a 2D OCT image 1210 and a spectrogram 1220 before the depth-directional movement of a mirror that is the measurement target is compensated in the full-field OCT system according to an embodiment of the present disclosure. The 2D OCT image 1210 is an x-axis and z-axis (axis in depth-direction) plane image of the measurement target. The 2D OCT image 1210 includes the depth-directional movement of the mirror as artifacts, so that the planar shape of the mirror is not clearly shown. Meanwhile, the spectrogram 1220 shows the depth-directional movement at each point in time where the wavelength of the wavelength-tunable laser is changed, based on one point 1211 on the mirror. That is, the depth-directional movement of the mirror is shown similar to a sine wave form in the spectrogram 1220.

Figure 13:
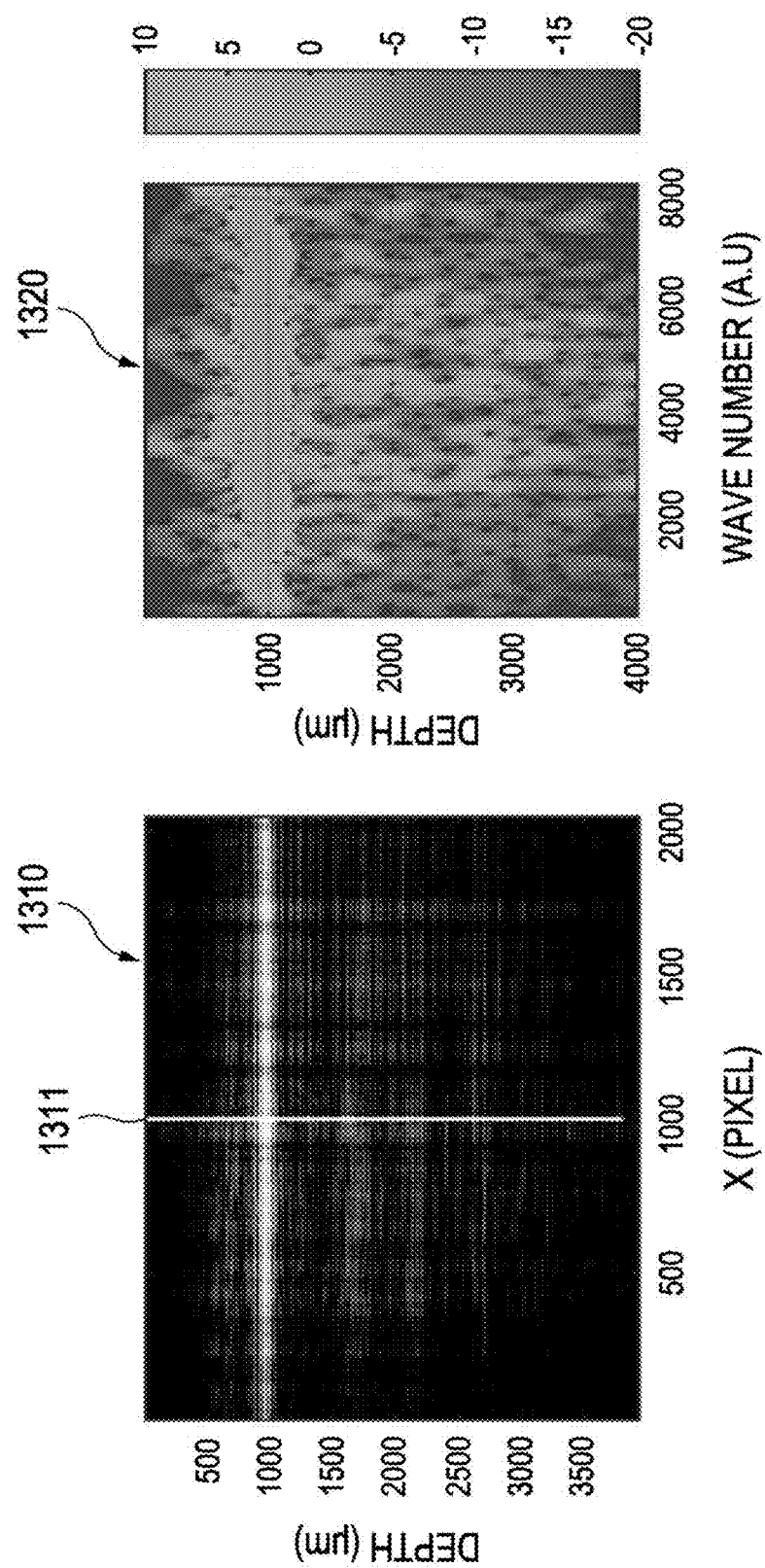
FIG. 13 shows a two-dimensional OCT image and a spectrogram after depth-directional movement of the mirror that is the measurement target is compensated for in the full-field OCT system according to an embodiment of the present disclosure.

FIG. 13 shows a 2D OCT image 1310 and a spectrogram 1320 after the depth-directional movement of a mirror that is the measurement target is compensated in the full-field OCT system according to an embodiment of the present disclosure. In the 2D OCT image 1310, the depth-directional movement of the mirror has been compensated and the planar shape of the mirror in the x-axis and z-axis plane is clearly shown. Since the depth-directional movement of the mirror has been compensated, the spectrogram 1320 obtained based on one point 1311 on the mirror shows that the position of the peak of an A-line profile is maintained at each point in time where the wavelength of the wavelength-tunable laser is changed.

Figure 14:
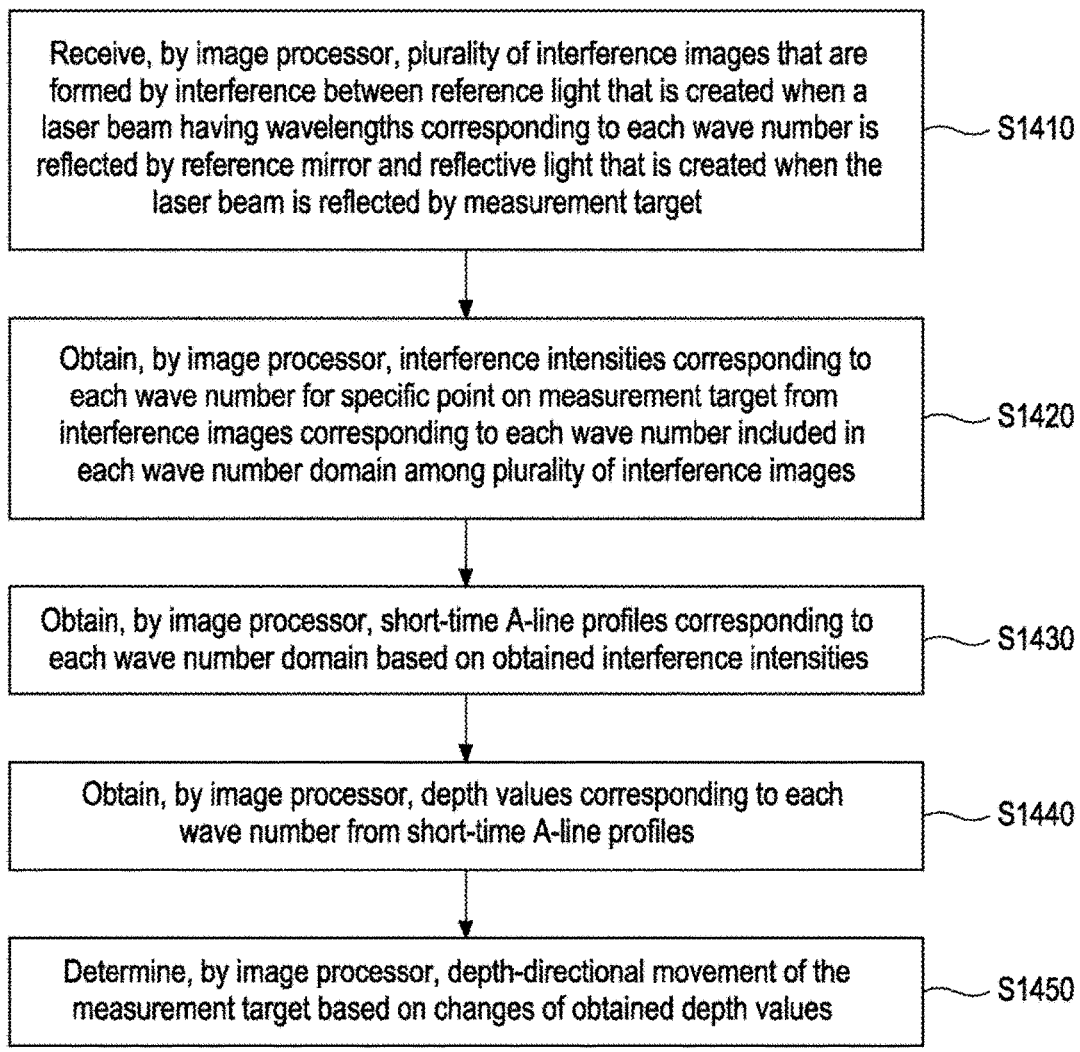
FIG. 14 is a flowchart showing a method of determining depth-directional movement of a measurement target in the full-field OCT system in accordance with an embodiment of the present disclosure.

FIG. 14 is a flowchart showing a method of determining depth-directional movement of the measurement target 450 in the full-field OCT system 400 in accordance with an embodiment of the present disclosure. Hereinafter, each step of the method of determining depth-directional movement of the measurement target 450 is described in detail with reference to the drawing.

First, in Step S1410, the image processor can receive a plurality of interference images created by interference between the reference light created when a laser beam having a wavelength corresponding to each wave number is reflected by the reference mirror, and the reflective light created when the laser beam is reflected by the measurement target. For example, with reference to FIG. 4, the image processor 480 can receive the plurality of interference images from the interferometer including the wavelength-tunable laser 410, the beam splitter 430, the reference mirror 440, the imaging device 460 etc. In this case, the interferometer can create the plurality of interference images that is formed by interference between the reference light created when the laser beam radiated from the wavelength-tunable laser 410 and having a wavelength corresponding to each wave number is reflected by the reference mirror 440 and the reflective light created when the laser beam from the wavelength-tunable laser 410 is reflected by the measurement target 450. According to an embodiment, the plurality of interference images can be created at each point in time where the wavelength of the wavelength-tunable laser 410 is sequentially changed.

When the plurality of interference images is received in Step S1410, the image processor, in Step S1420, can obtain interference intensities corresponding to each wave number for a specific point on the measurement target from interference images corresponding to each wave number included in each wave number domain of the received interference images. For example, the image processor 480 can extract interference images corresponding to each wave number included in sliding wave number domain windows of the received interference images by sequentially applying a sliding wave domain window having a predetermined size to the received interference images. The image processor 480 can obtain interference intensities corresponding to each wave number included in each wave number domain for the specific point on the measurement target 450 from the obtained interference images corresponding to each wave number included in each wave number domain.

Figure 15:
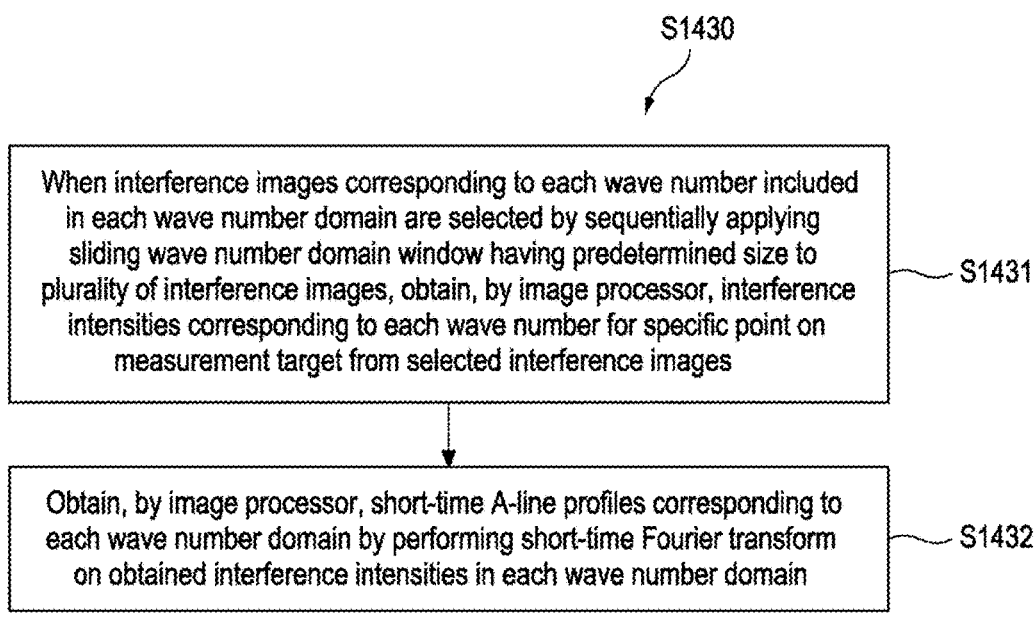
FIG. 15 is a flowchart showing a method of obtaining a plurality of short-time A-line profiles by means of an image processor in the full-field OCT system according to an embodiment of the present disclosure.

Next, in Step S1430, the image processor can obtain short-time A-line profiles corresponding to the wave number domains based on the obtained interference intensities. In detail, with reference to FIG. 15, in Step S1431, when interference images corresponding to each wave number included in each wave number domain are selected, the image processor can obtain interference intensities corresponding to the wave numbers for the specific point on the measurement target from the selected interference images by sequentially applying a sliding wave number domain window having a predetermined size to the received interference images.

For example, with reference to FIGS. 5 and 6, the image processor 480 sequentially applies the sliding wave number domain window 660 having a size 5 in a wave number domain to the plurality of interference images, whereby interference images corresponding to each wave number included in each wave number domain, in which a wave length is changed four times, can be selected. The image processor 480 can obtain interference intensities corresponding to each wave number included in each wave number domain for the specific point on the measurement target 450 from the selected interference images.

If the sliding wave number domain window 660 is applied to a wave number domain of k1 to k5, the image processor 480 can obtain the interference intensities 610, 620, 630, 640, and 650 from the interference images 510, 520, 530, 540, and 550 captured for a short time period while the wave number changes from k1 to k5. Thereafter, the image processor 480 can obtain interference intensities by applying the sliding wave number domain window 660 to the next wave number domain, that is, the wave number domain of k2 to k6 in accordance with a sequence where the wavelength of the wavelength-tunable laser 410 is changed. In the same manner, the image processor 480 can obtain interference intensities corresponding to each wave number included in the corresponding wave number domain by sequentially applying the sliding wave number domain window 660 to the plurality of interference images. In this case, the interference intensities can be obtained at the same point respectively corresponding to the specific point on the measurement target 450 in the interference images.

When interference intensities are obtained in Step S1431, the image processor 480, in Step S1432, can obtain short-time A-line profiles corresponding to the wave number domains by performing short-time Fourier transform on the obtained interference intensities in the wave number domains. For example, the image processor 480 can obtain short-time A-line profiles by performing short-time Fourier transform on interference intensities, which correspond to each wave number included in the wave number domain of the sliding wave number domain window 660, in the corresponding wave number domain. In detail, the image processor 480 can obtain the short-time A-line profiles by obtaining the short-time wave number domain profiles for the interference intensities obtained by sequentially applying the sliding wave number domain window 660 and by performing short-time Fourier transform on the obtained short-time wave number domain profiles respectively.

For example, with reference to FIG. 6, when the sliding wave number domain window 660 is applied to the wave number domain of k1 to k5, the image processor 480 can obtain a short-time wave number domain profile showing the wave number domain distribution of the interference intensities 610, 620, 630, 640, and 650 in the short-time wave number domain. The image processor 480 can obtain a short-time A-line profile from the short-time wave number domain profile by performing short-time Fourier transform on the wave number for this short-time wave number domain profile. In the same manner, the image processor 480 can obtain short-time wave number domain profiles respectively for interference intensities in obtained other short-time wave number domains by sequentially applying the sliding wave number domain window 660, and can obtain short-time A-line profiles by performing short-time Fourier transform on the wave number for the obtained short-time wave number domain profiles.

With reference to FIG. 14, in Step S1440, the image processor can obtain depth values corresponding to each wave number domain from each short-time A-line profile. For example, the image processor 480 can obtain depth values corresponding to the peaks of the short-time A-line profiles from each short-time A-line profile corresponding to the each wave number domain of the sliding wave number domain window. The obtained depth values may be the depth values at the specific point on the measurement target 450 at each points in time where the wavelength of the wavelength-tunable laser 410 is changed.

Next, in Step S1450, the image processor can determine depth-directional movement of the measurement target based on changes of the obtained depth values. For example, with reference to FIG. 9, the image processor 480 can determine depth-directional movement of the measurement target 450 while sweeping the wavelength of the wavelength-tunable laser 410 by observing changes of the depth values 910, 920, 930, 940, and 950 of the measurement target 450 corresponding to each point in time k3, k4, k5, k6, and k7 where the wavelength is changed.

Figure 16:
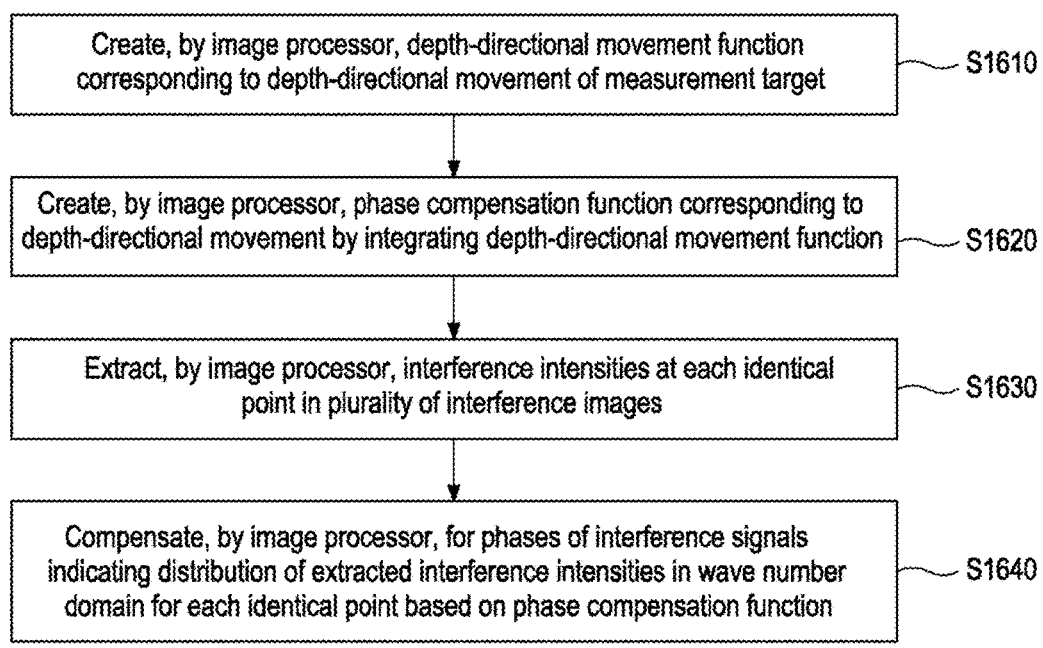
FIG. 16 is a flowchart showing a method of compensating for depth-directional movement of a measurement target in an OCT image in accordance with an embodiment of the present disclosure.

When the depth-directional movement of the measurement target 450 is determined in this way, the image processor 480 can compensate for the influence of the depth-directional movement of the measurement target 450 in an OCT image based on the depth-directional movement. In detail, with reference to FIG. 16, first in Step S1610, the image processor can create the depth-directional movement function corresponding to depth-directional movement of the measurement target. For example, with reference to FIG. 9, the image processor 480 can create the depth-directional movement function 960 by performing curve fitting on changes of the depth value (e.g. changes of the depth value to 910, 920, 930, 940, and 950) of the peak of an A-line profile according to a change in wave number (e.g., changes of the wave number to k3 to k4, k5, k6, and k7), in which the changes of the depth value correspond to the depth-directional movement of the measurement target 450 at each point in time where the wavelength is changed.

When the depth-directional movement function is created in Step S1610, the image processor, in Step S1620, can create the phase compensation function corresponding to the depth-directional movement by integrating the depth-directional movement function. When there is depth-directional movement of the measurement target 450, phases of the interference signals that are used to create an OCT image may be distorted by the depth-directional movement. The phase compensation function can show a degree of distortion of phases due to depth-directional movement of the measurement target 450 at each point in time where the wavelength is changed. The image processor 480 can create such a phase compensation function by integrating the depth-directional movement function.

Next, in Step S1630, the image processor can extract interference intensities at identical points in the plurality of interference images to obtain the object where depth-directional movement is to be compensated. According to an embodiment, an interference signal showing the distribution of interference intensities in a wave number domain may be the object where depth-directional movement is to be compensated. Accordingly, the image processor 480 can obtain all interference signals that can be created in a measurement domain of the measurement target 450 where depth-directional movement is to be compensated, by extracting interference intensities at each identical point in the plurality of interference images.

When interference intensities are extracted in Step S1630, the image processor, in Step S1640, can compensate for the phases of the interference signals indicating the distribution of the interference intensities, extracted for each identical point, in the wave number domain based on the phase compensation function. For example, if an interference signal before the phase is compensated is I(k), the interference signal after the phase is compensated is Icomp(k), and the phase compensation function is θ(k), the image processor 480 can compensate for the phase distortion of an interference signal through the following equation.

$$Icomp(k)=I(k)\cdot e-i\theta(k)$$

(where k is a wave number)

The image processor 480 can only compensate for the phase distortion of an interference signal at a point corresponding to one point of the measurement target 450 in an interference image through the equation above. The image processor 480 can obtain all interference signals that can be created in the measurement domain of the measurement target 450, using the interference intensities extracted for each identical point in Step S1630, and then can compensate for the phase distortion of all interference signals based on the phase compensation function. As described above, by compensating for the phase distortion of the interference signals at all points, the image processor 480 can create an OCT image where the influence by depth-direction movement is completely compensated.

<Measurement and Compensation of Horizontal Movement>

A method of measuring horizontal movement of the measurement target 450 and a method of compensating for the horizontal movement in an OCT image using the method of measuring the horizontal movement in the full-field OCT system 400 are described hereafter.

Horizontal movement of the measurement target 450 may be horizontal movement of the measurement target 450 while the full-field OCT system 400 obtains interference images at each point in time where the wavelength of the wavelength-tunable laser 410 is changed. If the measurement target 450 moves horizontally, different measurement portions of the measurement target 450 may be shown at identical points of interference images. Accordingly, if interference signals are obtained at identical points on interference images, the interference signals may partially include information about different measurement portions of the measurement target 450. Accordingly, if there is horizontal movement of the measurement target 450, the horizontal movement may appear in the form of after-images in the created OCT image.

Figure 17:
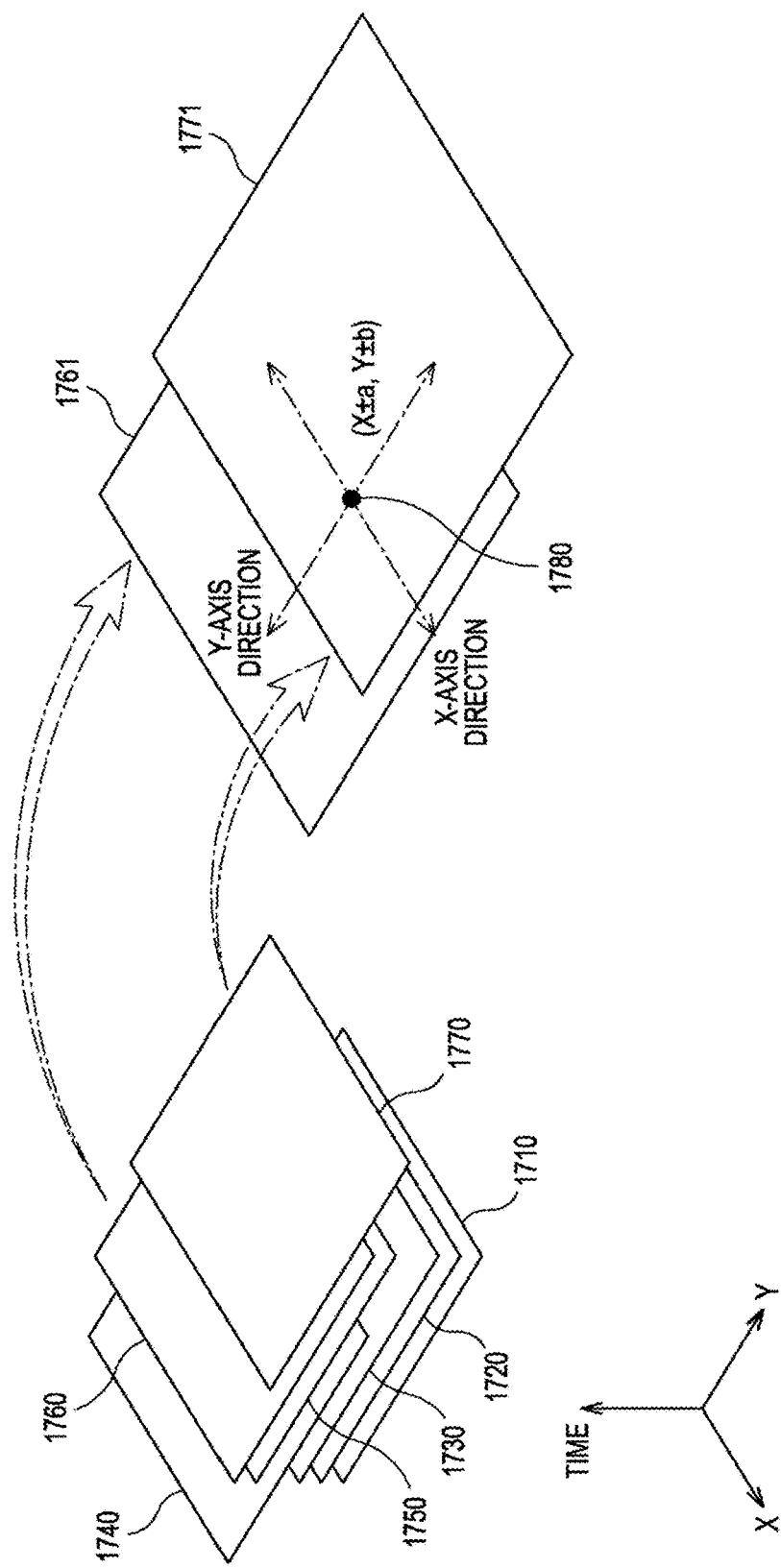
FIG. 17 is a drawing illustrating a method of determining horizontal movement of a measurement target and compensating for, based on the determined results, the horizontal movement in an OCT image in the full-field OCT system in accordance with an embodiment of the present disclosure.

For example, as illustrated in FIG. 17, when there is horizontal movement of the measurement target 450 while the wavelength of the wavelength-tunable laser 410 is changed, a portion 1740 and 1770 of the interference images 1710, 1720, 1730, 1740, 1750, 1760, and 1770 sequentially captured by the imaging device 460 may be taken as if the observation view has been moved. Accordingly, comparing the interference images 1710, 1720, 1730, 1750, and 1760 and the interference images 1740 and 1770 based on the same point in the interference images, different measurement portions of the measurement target 450 may be included in the interference images 1740 and 1770.

Figure 18:
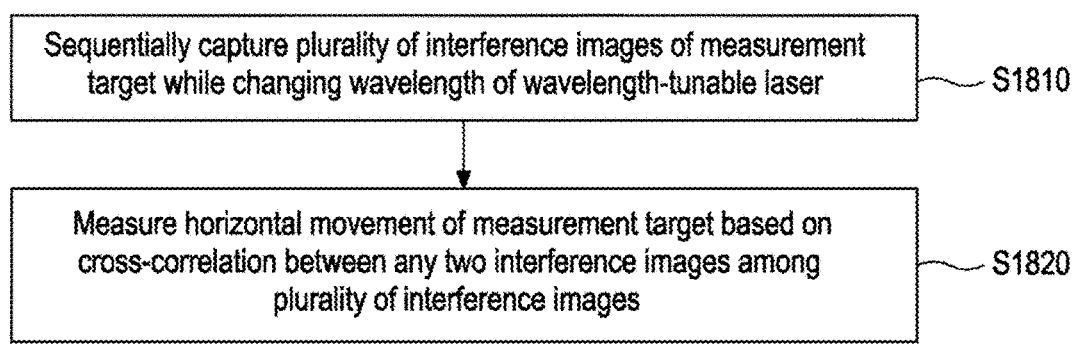
FIG. 18 is a flowchart showing a method of measuring horizontal movement of a measurement target in the full-field OCT system in accordance with an embodiment of the present disclosure.

FIG. 18 is a flowchart showing a method of determining horizontal movement of the measurement target 450 in the full-field OCT system 400 in accordance with an embodiment. The method of measuring horizontal movement for each step is described in detail hereafter.

First, in Step S1810, the image processor can sequentially capture the plurality of interference images of the measurement target while changing the wavelength of the wavelength-tunable laser. For example, with reference to FIGS. 4 and 17, while the image processor 480 changes the wavelength of the wavelength-tunable laser 410, it can sequentially create the plurality of interference images 1710 to 1770 that are formed by interference between the reference light created when light from the wavelength-tunable laser 410 is reflected by the reference mirror and the reflective light created when the light from the wavelength-tunable laser 410 is reflected by the measurement target 450.

When the plurality of interference images are created in Step S1810, the image processor, in Step S1820, can measure the horizontal movement of the measurement target based on cross-correlation between any two interference images among the plurality of interference images. For example, the image processor 480 can measure the horizontal movement of the measurement target 450 based on cross-correlation between any two interference images among the obtained interference images showing the horizontal movement.

According to an embodiment, when there is no horizontal movement, the cross-correlation between two interference images may be larger than the cross-correlation that is calculated when there is horizontal movement. Accordingly, based on this principle, the image processor 480 can determine the degree of horizontal movement of the measurement target 450.

In detail, the image processor 480 can horizontally move one of the two interference images by changing coordinate values of the interference image. The image processor 480 can obtain the coordinate values when the cross-correlation between the two interference images becomes the maximum while horizontally moving one of the two interference images. Accordingly, the image processor 480 can determine the degree of horizontal movement of the measurement target 450 based on the difference between the coordinate values when the cross-correlation is maximum and the coordinate values before the horizontal movement.

In accordance with an embodiment, when the horizontal movement between two continuous interference images included in all sequentially captured interference images is completely measured, the image processor 480 can determine the relative movement of the measurement target 450 shown in all interference images based on any one of the interference images.

The method of measuring horizontal movement of the measurement target 450 based on the cross-correlation between any two images is described hereafter with reference to FIG. 17.

First, it may be assumed that the two arbitrary interference images among the interference images shown at the left side of FIG. 17 for measuring the horizontal movement are the interference image 1760 and the interference image 1770. Further, for the convenience of description, an interference image 1761 and an interference image 1771, formed by enlarging the interference image 1760 and the interference image 1770 respectively, are illustrated at the right side of FIG. 17. It may be assumed that, in the interference images 1760 and 1770, the interference image 1770 is an interference image captured when there was horizontal movement of the measurement target 450.

The image processor 480 can calculate the cross-correlation between the two interference images 1761 and 1771 while horizontally moving the coordinate values of one interference image 1771 of the two interference images 1761 and 1771 with respect to the other interference image 1761 in the X-axis and Y-axis directions. Accordingly, the image processor 480 can obtain the coordinate values of the interference image 1771 when the cross-correlation of the two interference images 1761 and 1771 becomes maximum. The image processor 480 can calculate the cross-correlation between the two interference images while horizontally moving one interference image 1771 as a whole with respect to the other interference image 1761, but it may extract only a characteristic domain of the interference image 1771 and calculate the cross-correlation with the interference image 1761 while horizontally moving this domain. The image processor 480 can calculate the degree of horizontal movement of the measurement target 450 based on the difference between the coordinate values before and after moving the interference image 1771 as a whole or a partial domain of the interference image 1771.

For example, it may be assumed that the coordinate of one horizontal point 1780 in the interference image 1771 is (X, Y). Further, it may be assumed that the cross-correlation between the interference image 1761 and the interference image 1771 becomes maximum when the coordinate values of the interference image 1771 are moved by a and b respectively in the X-axis and Y-axis directions with the interference image 1761 fixed. In this case, the image processor 480 can determine that the measurement target 450 shown in the interference image 1771 has been moved with a change in the X-axis direction of –a and a change in Y-axis direction of –b with respect to the measurement target 450 shown in the interference image 1761.

Figure 19:
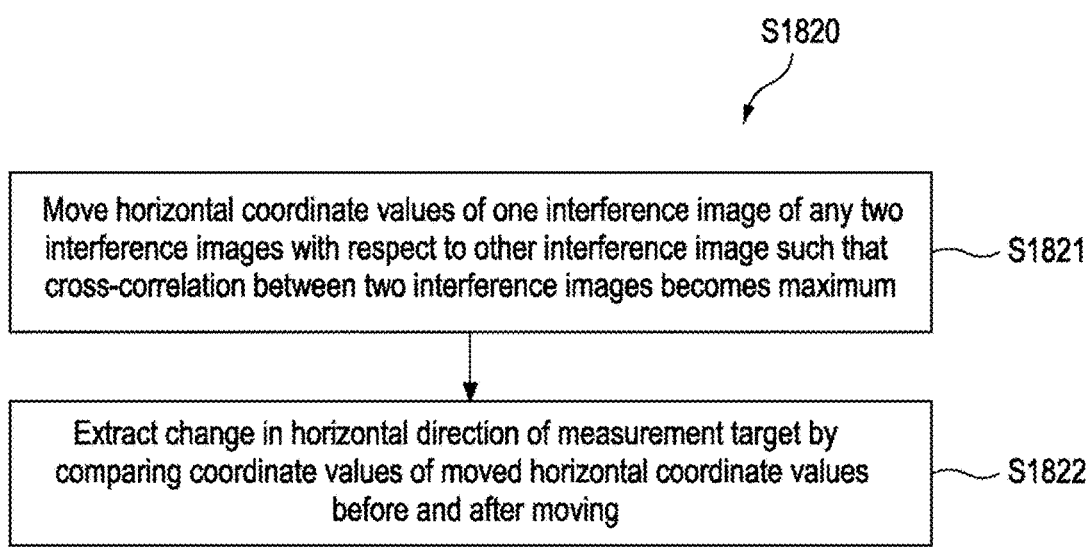
FIG. 19 is a flowchart showing a method of measuring horizontal movement of a measurement target based on cross-correlation between interference images in the full-field OCT system in accordance with an embodiment of the present disclosure.

FIG. 19 is a flowchart showing the method of measuring horizontal movement of the measurement target 450 based on the cross-correlation between interference images in the full-field OCT system 400 in accordance with an embodiment of the present disclosure. First, in Step S1821, the image processor can move the horizontal coordinate values of one interference image of any two interference images with respect to the other interference image such that the cross-correlation between any two interference images becomes maximum. Thereafter, in Step S1822, the image processor can extract the change in horizontal direction of the measurement target by comparing the coordinate values of the moved horizontal coordinate values before and after moving.

Figure 20:
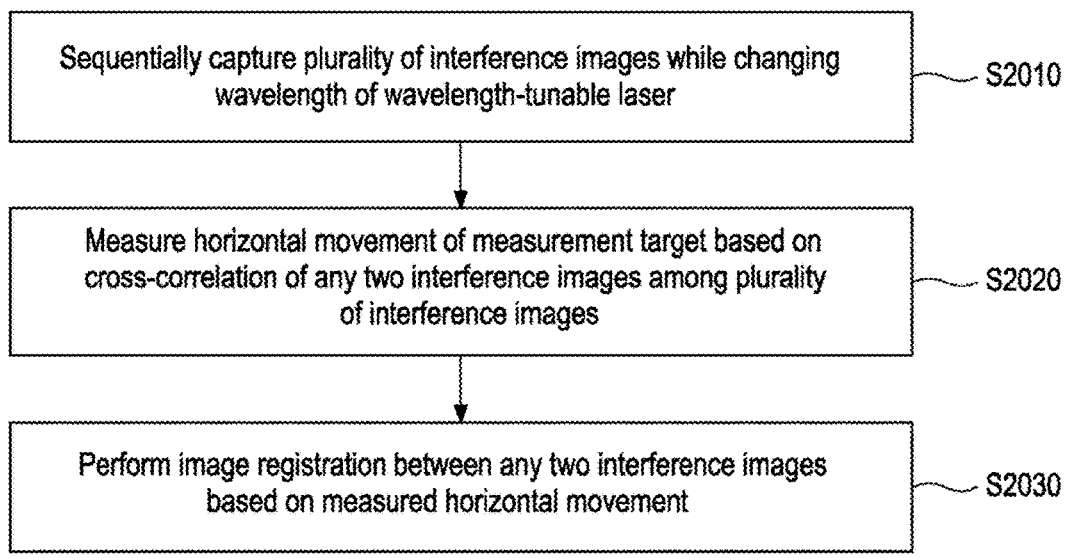
FIG. 20 is a flowchart showing a method of compensating for horizontal movement of a measurement target in an OCT image in accordance with an embodiment of the present disclosure.

Next, the method of compensating for horizontal movement in an OCT image based on the horizontal movement of the measurement target 450 is described hereafter. FIG. 20 is a flowchart showing the method of compensating for horizontal movement of the measurement target 450 in an OCT image in accordance with an embodiment of the present disclosure. Horizontal movement of the measurement target 450 can be measured in the same manner as the method described with reference to FIG. 18. Accordingly, the image processor, as a process of measuring the horizontal movement of the measurement target 450, can sequentially capture the plurality of interference images while changing the wavelength of the wavelength-tunable laser in Step S2010. Further, the image processor can, in Step S2020, measure the horizontal movement of the measurement target based on the cross-correlation between any two interference images among the plurality of interference images.

As described above, when the horizontal movement of the measurement target is measured through Step S2010 and Step S2020, the image processor, in Step S2030, can perform image registration between any two interference images based on the measured horizontal movement to compensate for the horizontal movement of the measurement target. In detail, the image processor 480 can extract a change in horizontal direction based on the measured horizontal movement and perform the image registration between any two interference images based on the extracted change.

The "image registration" may mean a processing technique for obtaining images in one coordinate system by transforming images having different coordinate systems. The correspondence between one image and another image can be determined through image registration. For example, with reference to FIG. 17, even if measurement targets 450 are not at the same position in the interference image 1761 and the interference image 1771 due to horizontal movement of the measurement target 450, it can be determined how the coordinate values of the same target in each interference image correspond to each other through image registration. Accordingly, when the change in horizontal direction between any two interference images is extracted, the image processor 480 1) can determine the correspondence between the coordinate values of the same target included in one interference image and another interference image through image registration, and 2) when matching the coordinates between the interference image that has become the reference and the other interference image by changing the coordinate values by the extracted change in horizontal direction, 3) the horizontal movement of the measurement target 450 included in any two interference images can be compensated. The image processor 480 can create an OCT image where the horizontal movement has been compensated, by compensating the horizontal movement of the measurement target 450 using the method above for all sequentially captured plurality of interference images.

According to a method of measuring and compensating for the horizontal movement of the measurement target 450 pursuant to an embodiment of the present disclosure, it is possible to measure and correct the horizontal movement using only the information included in interference images. Accordingly, the process of measuring and compensating for horizontal movement may not influence the process of measuring and compensating for depth-directional movement. According to an embodiment, if the measurement target 450 has moved in the depth direction and the horizontal direction, the image processor 480 can perform the process of measuring and compensating for the horizontal movement and then the process of measuring and compensating for the depth-directional movement. By compensating the horizontal and depth-directional movement of the measurement target 450 in this sequence, the image processor 480 can completely compensate the influence of movement of the measurement target 450 in a three-dimensional space in an OCT image.

Although the methods above were described using specific embodiments, the methods can be implemented by computer-readable code on a computer-readable storage medium. The computer-readable storage medium includes all kinds of storage devices that store data that can be read by a computer system. The computer-readable storage medium, for example, may be a ROM, a RAM, a CD-ROM, a magnetic tape, a floppy disk, and an optical data storage device, and includes the implementation by a carrier wave (e.g. transmission via internet). Further, the computer-readable storage medium may be distributed on computer systems that are connected via a network and may store and execute code that can be read by computers in a decentralized manner. Further, functional programs, codes, and code segments for implementing the embodiments above may be easily inferred by programmers in the technical field to which this disclosure pertains.

Although the present disclosure was described in relation to some embodiments, it should be understood that the present disclosure may be changed and modified in various ways without departing from the spirit and scope of the present disclosure as understood by those skilled in the art. The changes and modifications should be understood as being included in scope of the claims attached to this description.

What is claimed is:

1. A full-field Optical Coherence Tomography (OCT) system comprising an image processor that determines depth-directional movement of a measurement target and compensates the depth-directional movement of the measurement target based on a plurality of interference images that are formed by interference between reference light, that is created when a laser beam having wavelengths corresponding to each wave number is reflected by a reference mirror, and reflective light that is created when the laser beam is reflected by the measurement target, wherein the image processor is configured to:
obtain interference intensities corresponding to each wave number for a specific point on the measurement target, from interference images corresponding to each wave number included in each wave number domain among the plurality of interference images;
obtain short-time A-line profiles corresponding to each wave number domain based on the obtained interference intensities;
obtain depth values corresponding to each wave number domain from each short-time A-line profile; and
determine the depth-directional movement of the measurement target based on changes of the obtained depth values.

2. The full-field OCT system of claim 1, wherein when the interference images corresponding to each wave number included in each wave number domain are selected by sequentially applying a sliding wave number domain window having a predetermined size to the plurality of interference images, the image processor is further configured to:
obtain the interference intensities corresponding to each wave number for the specific point on the measurement target from the selected interference images; and
obtain the short-time A-line profiles corresponding to each wave number domain by performing short-time Fourier transform on the obtained interference intensities in each wave number domain.

3. The full-field OCT system of claim 1, wherein the depth values correspond to each peak of the short-time A-line profiles.

4. The full-field OCT system of claim 1, wherein the image processor is further configured to:
create a depth-directional movement function corresponding to depth-directional movement of the measurement target;
create a phase compensation function corresponding to the depth-directional movement by integrating the depth-directional movement function;

extract interference intensities at each identical point in the plurality of interference images; and
compensate for the depth-directional movement of the measurement target by compensating for phases of the interference signals indicating the distribution of the extracted interference intensities in a wave number domain for each identical point based on the phase compensation function.

5. The full-field OCT system of claim 1, further comprising:
an interferometer configured to create the plurality of interference images corresponding to each wave number, wherein the interferometer includes:
a wavelength-tunable laser configured to radiate a laser beam having wavelengths corresponding to each wave number by tuning a wavelength;
a reference mirror;
a beam splitter configured to transmit a portion of the laser beam from the wavelength-tunable laser toward the measurement target and reflect the other portion of the laser beam toward the reference mirror; and
an imaging device configured to create the plurality of interference images by receiving the reflective light and the reference light from the beam splitter.

6. A method of determining depth-directional movement of a measurement target and compensating for the depth-directional movement of the measurement target in a full-field OCT system, the method comprising:
receiving, by an image processor, a plurality of interference images that are formed by interference between reference light that is created when a laser beam having wavelengths corresponding to each wave number is reflected by a reference mirror and reflective light that is created when the laser beam is reflected by the measurement target;
obtaining, by the image processor, interference intensities corresponding to each wave number for a specific point on the measurement target from interference images corresponding to each wave number included in each wave number domain among the plurality of interference images;
obtaining, by the image processor, short-time A-line profiles corresponding to each wave number domain based on the obtained interference intensities;
obtaining, by the image processor, depth values corresponding to each wave number domain from the short-time A-line profiles; and
determining, by the image processor, the depth-directional movement of the measurement target based on changes of the obtained depth values.

7. The method of claim 6, wherein when the interference images corresponding to each wave number included in each wave number domain are selected by sequentially applying a sliding wave number domain window having a predetermined size to the plurality of interference images, the act of obtaining, by the image processor, the short-time A-line profiles includes:
obtaining, by the image processor, the interference intensities corresponding to each wave number for the specific point on the measurement target from the selected interference images; and
obtaining, by the image processor, the short-time A-line profiles corresponding to each wave number domain by performing short-time Fourier transform on the obtained interference intensities in the wave number domains.

8. The method of claim 6, further comprising:
creating, by the image processor, a depth-directional movement function corresponding to the depth-directional movement of the measurement target;
creating, by the image processor, a phase compensation function corresponding to the depth-directional movement by integrating the depth-directional movement function;
extracting, by the image processor, interference intensities at each identical point in the plurality of interference images; and
compensating, by the image processor, for phases of interference signals indicating distribution of the extracted interference intensities in the wave number domain for each identical point based on the phase compensation function.

9. A computer-readable storage medium storing a program including commands for performing each step of the method of determining depth-directional movement of a measurement target and compensating for the depth-directional movement of the measurement target in a full-field OCT system according to claim 6.

* * * * *